US011547294B2

(12) United States Patent
Fukuma et al.

(10) Patent No.: US 11,547,294 B2
(45) Date of Patent: Jan. 10, 2023

(54) OPHTHALMIC APPARATUS, CONTROLLING METHOD THEREOF, AND RECORDING MEDIUM

(71) Applicant: TOPCON CORPORATION, Tokyo (JP)

(72) Inventors: Yasufumi Fukuma, Wako (JP); Takefumi Hayashi, Wako (JP); Yoko Tatara, Kita-ku (JP)

(73) Assignee: TOPCON CORPORATION, Tokyo (JP)

(*) Notice: Subject to any disclaimer, the term of this patent is extended or adjusted under 35 U.S.C. 154(b) by 663 days.

(21) Appl. No.: 16/568,262

(22) Filed: Sep. 12, 2019

(65) Prior Publication Data
US 2020/0085292 A1 Mar. 19, 2020

(30) Foreign Application Priority Data
Sep. 18, 2018 (JP) .............................. JP2018-173777

(51) Int. Cl.
*A61B 3/10* (2006.01)
*A61B 3/00* (2006.01)
*A61B 3/15* (2006.01)

(52) U.S. Cl.
CPC ............ *A61B 3/102* (2013.01); *A61B 3/0025* (2013.01); *A61B 3/152* (2013.01)

(58) Field of Classification Search
CPC .. A61B 3/102; A61B 3/14; A61B 3/12; A61B 3/0025; A61B 3/1225; A61B 3/113;
(Continued)

(56) References Cited

U.S. PATENT DOCUMENTS

RE46,044 E 6/2016 Arai et al.
2005/0018132 A1 1/2005 Fukuma et al.
(Continued)

FOREIGN PATENT DOCUMENTS

CN 101049229 A 10/2007
CN 101460114 A 6/2009
(Continued)

OTHER PUBLICATIONS

Schmid, Gregor F., "Axial and peripheral eye length measured with optical low coherence reflectometry", Journal of Biomedical Optics, Oct. 2003, pp. 655-662.
(Continued)

*Primary Examiner* — Brandi N Thomas
(74) *Attorney, Agent, or Firm* — Xsensus LLP

(57) ABSTRACT

An ophthalmic apparatus of an exemplary aspect performs the first and second OCT scans on a subject's eye. The first OCT scan is performed on the first region including the first site of the subject's eye, and the second OCT scan is performed on the second region including the second site. The ophthalmic apparatus acquires the first deviation information of the subject's eye prior to the first OCT scan and performs alignment, and also acquires the second deviation information of the subject's eye prior to the second OCT scan and performs alignment. The ophthalmic apparatus calculates the distance between the first site and the second site based on the first data acquired through the first OCT scan and second data acquired through the second OCT scan.

9 Claims, 12 Drawing Sheets

(58) Field of Classification Search

CPC ......... A61B 3/0033; A61B 3/152; A61B 3/10;
A61B 5/0066; A61B 3/117; A61B
3/0083; A61B 2090/3937; A61B 3/0075;
A61B 3/0016; A61B 3/0091; A61B
3/0058; A61B 3/13; A61B 3/0041; A61B
18/20; A61B 3/0008; A61B 3/1005; A61B
3/107; A61B 5/0073; A61B 2017/00057;
A61B 2090/378; A61B 2560/0233; A61B
3/18; A61B 3/005; A61B 3/1025; A61B
3/145; A61B 2090/3983; A61B 5/0064;
A61B 5/70; A61B 2034/2065; A61B
2090/3735; A61B 3/132; A61B 3/135;
A61B 5/0035; A61B 5/055; A61B 5/064;
A61B 8/48; A61B 3/00; A61B 3/101;
A61B 3/11; A61B 3/112; A61B 5/7257;
A61B 5/7267; A61B 8/10; A61B 90/20;
A61B 2018/00351; A61B 2018/00446;
A61B 2018/00517; A61B 2018/00642;
A61B 2018/20351; A61B 2018/20355;
A61B 3/1015; A61B 3/103; A61B
3/1233; A61B 3/1241; A61F 2009/00851;
A61F 2009/0087; A61F 9/00825; A61F
9/008; A61F 2009/00872; A61F
2009/0088; A61F 2009/00882; A61F
2009/00897; A61F 9/009; A61F
2009/00863; A61F 2009/00844; A61F
2009/00855; A61F 9/00827; A61F
9/00821; A61F 2009/00887; A61F
2009/00846; A61F 2009/00889; A61F
9/00823; A61F 9/00836; A61F 9/0084;
A61F 2009/00895; A61F 9/00829; A61F
9/00834; A61F 9/00838; A61F
2009/00853; A61F 2009/00865; A61F
2009/00891; A61F 2009/00878; A61F
9/00736; A61F 9/0079; A61F 2/16; G06T
2207/30041; G06T 2207/10101; G06T
2200/24; G06T 7/0014; G06T
2207/20036; G06T 2207/20081; G06T
2207/20084; G06T 2207/10016; G06T
2207/20224; G06T 7/248; G06T 7/37;
G06T 2207/10024; G06T 2207/10048;
G06T 2207/20056; G06T 5/002; G06T
5/004; G06T 5/007; G06T 5/009; G06T
5/50; G06T 7/0012; G06T 7/20; G06T
7/73; G06T 7/74; G06T 11/001; G06T
11/008; G06T 11/60; G06T 2207/30168;
G06T 2210/41; G06T 5/001; G06T 7/12;
G01B 9/02091; G01B 9/0203; G01B
9/02044; G01B 9/02004; G01B 9/02035;
G01B 9/02; G01B 9/02089; G01B
9/02075; G01B 9/02078; G01B 9/02083;
G01B 9/02055; G01B 9/02068; G01B
9/02087

See application file for complete search history.

(56) References Cited

U.S. PATENT DOCUMENTS

| | | |
|---|---|---|
| 2007/0016234 A1 | 1/2007 | Daxer |
| 2007/0236661 A1 | 10/2007 | Fukuma et al. |
| 2009/0064601 A1 | 3/2009 | Kroes |
| 2009/0076601 A1 | 3/2009 | Daxer |
| 2009/0240327 A1 | 9/2009 | Daxer |
| 2009/0244485 A1 | 10/2009 | Walsh |
| 2011/0032480 A1* | 2/2011 | Rathjen ............... A61B 3/1005 351/205 |
| 2011/0098790 A1 | 4/2011 | Daxer |
| 2011/0255054 A1 | 10/2011 | Hacker et al. |
| 2011/0299034 A1 | 12/2011 | Walsh |
| 2011/0313344 A1 | 12/2011 | Daxer |
| 2012/0095553 A1 | 4/2012 | Daxer |
| 2012/0174497 A1 | 7/2012 | Kroes |
| 2012/0200821 A1 | 8/2012 | Arai et al. |
| 2013/0041461 A1 | 2/2013 | Daxer |
| 2013/0201449 A1 | 8/2013 | Walsh |
| 2014/0098345 A1 | 4/2014 | Cai et al. |
| 2014/0268057 A1 | 9/2014 | Hacker et al. |
| 2014/0333895 A1 | 11/2014 | Satake |
| 2015/0085252 A1 | 3/2015 | Fujimura et al. |
| 2015/0085253 A1 | 3/2015 | Walsh |
| 2015/0138503 A1 | 5/2015 | Walsh |
| 2015/0208916 A1 | 7/2015 | Hayashi |
| 2015/0245765 A1 | 9/2015 | Fujii et al. |
| 2015/0250583 A1 | 9/2015 | Rosen et al. |
| 2016/0038023 A1* | 2/2016 | Endo ................... A61B 3/10 351/221 |
| 2016/0302659 A1 | 10/2016 | Boss et al. |
| 2016/0345822 A1 | 12/2016 | Fujimura et al. |
| 2017/0049318 A1 | 2/2017 | Walsh |
| 2017/0069105 A1 | 3/2017 | Kano et al. |
| 2017/0100033 A1 | 4/2017 | Sakurada |
| 2017/0119247 A1 | 5/2017 | Walsh |
| 2017/0311796 A1 | 11/2017 | Walsh |
| 2018/0140183 A1 | 5/2018 | Fukasawa et al. |
| 2018/0310819 A1 | 11/2018 | Boss et al. |
| 2019/0090733 A1 | 3/2019 | Walsh |
| 2019/0313894 A1 | 10/2019 | Kano et al. |
| 2020/0113430 A1 | 4/2020 | Boss et al. |

FOREIGN PATENT DOCUMENTS

| | | | |
|---|---|---|---|
| CN | 103764014 A | 4/2014 | |
| CN | 203643682 U | 6/2014 | |
| CN | 103892791 A | 7/2014 | |
| CN | 103976707 A | 8/2014 | |
| CN | 105919550 A | 9/2016 | |
| CN | 107567305 A | 1/2018 | |
| DE | 10 2008 063 225 A1 | 7/2010 | |
| EP | 1 444 945 A1 | 8/2004 | |
| EP | 2 455 799 A1 | 5/2012 | |
| EP | 3 081 146 A1 | 10/2016 | |
| JP | 2002-186584 A | 7/2002 | |
| JP | 2008-188047 A | 8/2008 | |
| JP | 2009-112431 A | 5/2009 | |
| JP | 2012-075640 A | 4/2012 | |
| JP | 2012-148032 A | 8/2012 | |
| JP | 2013-248376 A | 12/2013 | |
| JP | 2015-139512 A | 8/2015 | |
| JP | 2015-160103 A | 9/2015 | |
| JP | 2016-19634 A | 2/2016 | |
| JP | 2016-028682 A | 3/2016 | |
| JP | 2016-32609 A | 3/2016 | |
| JP | 2016-054854 A | 4/2016 | |
| JP | 2018089082 | * 12/2016 | ............ A61B 3/107 |
| JP | 2017-47127 A | 3/2017 | |
| JP | 2017-63978 A | 4/2017 | |
| JP | 2017-74115 A | 4/2017 | |
| JP | 2017-184874 A | 10/2017 | |
| JP | 2017-225638 A | 12/2017 | |
| JP | 2018-50922 A | 4/2018 | |
| JP | 2018-114230 A | 7/2018 | |
| JP | 2018-126257 | 8/2018 | |
| WO | 2010/117386 A1 | 10/2010 | |
| WO | 2013/159280 A1 | 10/2013 | |

OTHER PUBLICATIONS

Xin, Chen et al., "The influence of persistent high intraocular pressure on wavefront aberration", Opthalmol CHN, 2007, vol. 16, No. 4, 18 pp (with Machine translation by Google).

(56) References Cited

OTHER PUBLICATIONS

Chinese Office Action dated Aug. 26, 2021, in corresponding Chinese Patent Application No. 201910866660.0 (with Machine translation by Global Dossier).
Partial European Search Report dated Feb. 14, 2020 in European Patent Application No. 19195478.3, 12 pages.
Office Action dated Mar. 7, 2022 in Chinese Patent Application No. 201910866660.0, 10 pages.
Japanese Office Action dated Aug. 9, 2022 in corresponding Japanese Patent Application No. 2018-173777 (with machine-generated English translation), 9 pages.

\* cited by examiner

OPHTHALMIC APPARATUS, CONTROLLING METHOD THEREOF, AND RECORDING MEDIUM

CROSS-REFERENCE TO RELATED APPLICATION

This application is based upon and claims the benefit of priority from Japanese Patent Application No. 2018-173777, filed Sep. 18, 2018; the entire contents of which are incorporated herein by reference.

FIELD

Embodiments described herein relate to an ophthalmic apparatus, a controlling method thereof, and a recording medium.

BACKGROUND

Ophthalmic apparatuses capable of axial length measurement are known. For example, Japanese Unexamined Patent Application Publication No. 2016-19634 discloses an axial length measurement technique using optical coherence tomography (OCT). Axial length is defined as the distance between the corneal apex and the macula (fovea centralis). Axial length is one of useful intraocular parameters in selection of the power of an intraocular lens before cataract surgery, in checking of axial ametropia (axial refractive abnormality), etc.

Since axial length is defined as the distance between the corneal apex and the macula as described above, both the corneal position and the retinal position are required for axial length measurement. Regarding the invention disclosed in Japanese Unexamined Patent Application Publication No. 2016-19634, there is a time difference between the first measurement for determining the corneal position and the second measurement for determining the retinal position. Here, the first measurement includes an OCT scan of anterior eye segment mode and the second measurement includes an OCT scan of posterior eye segment mode. Therefore, if a subject's eye moves between the first measurement and the second measurement, there is a possibility that axial length cannot be measured accurately. In particular, movement in a direction orthogonal to the depth direction of the subject's eye may greatly reduce the reliability of the measured value of axial length.

DETAILED DESCRIPTION

Figure 1:
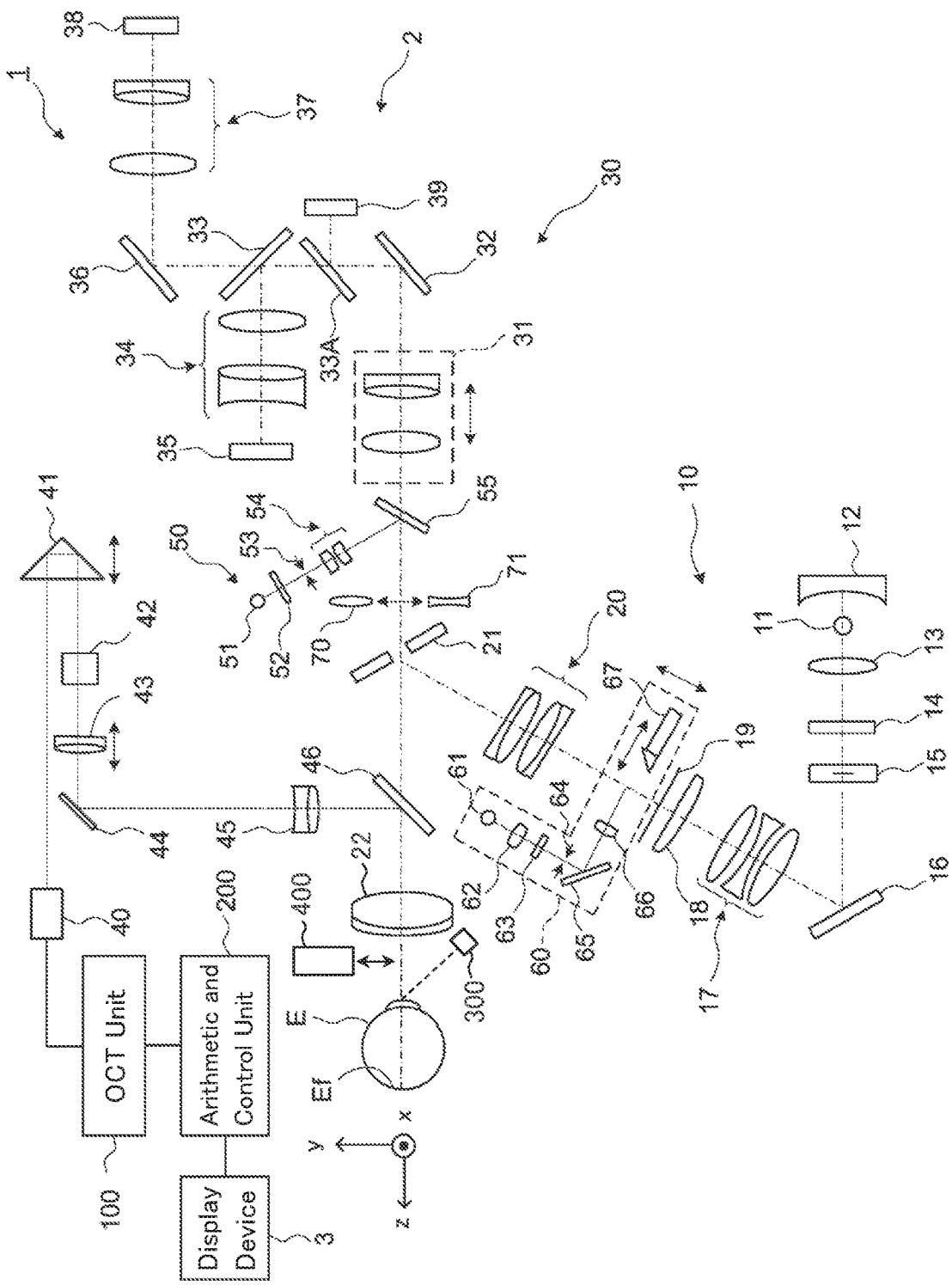
FIG. 1 is a schematic diagram illustrating an example of the configuration of an ophthalmic apparatus according to an exemplary embodiment.

One object of exemplary embodiments is to provide a technique capable of performing highly reliable axial length measurement regardless of the movement of the subject's eye.

The first aspect of the exemplary embodiments is an ophthalmic apparatus comprising: a scanner that applies an optical coherence tomography (OCT) scan to a subject's eye; a movement mechanism that moves at least part of the scanner; a deviation detector that measures deviation of the subject's eye with respect to a predetermined reference position; scan controlling circuitry that performs first scan control of causing the scanner to perform an OCT scan on a first region including a first site of the subject's eye, and second scan control of causing the scanner to perform an OCT scan on a second region including a second site different from the first site; alignment controlling circuitry that performs first alignment control of controlling the movement mechanism based on first deviation information of the subject's eye acquired by the deviation detector prior to the first scan control, and second alignment control of controlling the movement mechanism based on second deviation information of the subject's eye acquired by the deviation detector prior to the second scan control; and distance calculating circuitry that calculates a distance between the first site and the second site based on first data acquired by the scanner under the first scan control and second data acquired by the scanner under the second scan control.

The second aspect of the exemplary embodiments is the ophthalmic apparatus of the first aspect, wherein the scanner includes: an interference optical system that includes a measurement arm that guides measurement light to the subject's eye and a reference arm that guides reference light; and an arm length changer that is provided in at least one of the measurement arm and the reference arm, and changes an arm length under control of the scan controlling circuitry. Further, the distance calculating circuitry calculates a difference between a first arm length applied at a time of the first scan control and a second arm length applied at a time of the second scan control, analyzes the first data to specify a first position corresponding to the first site, analyzes the second data to specify a second position corresponding to the second site, and calculates the distance based on the difference, the first position, and the second position.

The third aspect of the exemplary embodiments is an ophthalmic apparatus comprising: a scanner that applies an optical coherence tomography (OCT) scan to a subject's eye; a deviation detector that measures deviation of the subject's eye with respect to a predetermined reference position; scan controlling circuitry that performs first scan control of causing the scanner to perform an OCT scan on a first region including a first site of the subject's eye, and second scan control of causing the scanner to perform an OCT scan on a second region including a second site different from the first site; and distance calculating circuitry that calculates a distance between the first site and the second site, based on at least one of first deviation information of the subject's eye acquired by the deviation detector in response to the first scan control and second deviation information of the subject's eye acquired by the deviation detector in response to the second scan control, first data acquired by the scanner under the first scan control, and second data acquired by the scanner under the second scan control.

The fourth aspect of the exemplary embodiments is the ophthalmic apparatus of the third aspect, wherein the deviation detector acquires one deviation information in response to one of the first scan control and the second scan control, and acquires another deviation information prior to an other of the first scan control and the second scan control. Further, the ophthalmic apparatus further comprises: a movement mechanism that moves at least part of the scanner; and alignment controlling circuitry that performs alignment control of controlling the movement mechanism based on the another deviation information prior to the other of the first scan control and the second scan control. In addition, the distance calculating circuitry calculates the distance based on the one deviation information, the first data, and the second data.

The fifth aspect of the exemplary embodiments is the ophthalmic apparatus of the third or fourth aspect, wherein the scanner includes: an interference optical system that includes a measurement arm that guides measurement light to the subject's eye, and a reference arm that guides reference light; and an arm length changer that is provided in at least one of the measurement arm and the reference arm, and changes an arm length under control of the scan controlling circuitry. Further, the distance calculating circuitry calculates a difference between a first arm length applied at a time of the first scan control and a second arm length applied at a time of the second scan control, analyzes the first data to specify a first position corresponding to the first site, analyzes the second data to specify a second position corresponding to the second site, and calculates the distance based on the difference, the first position, the second position, and at least one of the first deviation information and the second deviation information.

The sixth aspect of the exemplary embodiments is the ophthalmic apparatus of the fifth aspect, wherein the distance calculating circuitry calculates a provisional distance between the first site and the second site based on the difference, the first position, and the second position, and calculates the distance based on the provisional distance, at least one of the first deviation information and the second deviation information, and corneal curvature radius of the subject's eye acquired in advance.

The seventh aspect of the exemplary embodiments is the ophthalmic apparatus of the sixth aspect, wherein the distance calculating circuitry calculates the distance between the first site and the second site by using the following arithmetic formula: $AL = (r - r*\cos(\arcsin(h/r))) + AL_m * \cos(\arcsin(h/AL_m))$, where AL is the distance between the first site and the second site, $AL_m$ is the provisional distance, h is the first deviation information or the second deviation information, and r is the corneal curvature radius.

The eighth aspect of the exemplary embodiments is the ophthalmic apparatus of any one of the first to seventh aspects, wherein the scan controlling circuitry causes the scanner to perform a plurality of OCT scans in at least one of the first scan control and the second scan control, and the distance calculating circuitry acquires a single piece of data from a data group acquired by the plurality of OCT scans, and calculates the distance using the single piece of data.

The ninth aspect of the exemplary embodiments is the ophthalmic apparatus of the eighth aspect, wherein the distance calculating circuitry generates the single piece of data by averaging the data group.

The tenth aspect of the exemplary embodiments is the ophthalmic apparatus of any one of the first to seventh aspects, wherein the scan controlling circuitry causes the scanner to perform an OCT scan on a three dimensional region of the subject's eye in at least one of the first scan control and the second scan control, and the distance calculating circuitry analyzes data acquired by the OCT scan on the three dimensional region to specify a feature position corresponding to a feature point of the subject's eye, and calculates a length of a line segment whose one end is placed at the feature position, as the distance.

The eleventh aspect of the exemplary embodiments is the ophthalmic apparatus of the tenth aspect, wherein the scan controlling circuitry causes the scanner to perform an OCT scan on a three dimensional region including at least part of a corneal surface of the subject's eye in the first scan control, and the distance calculating circuitry analyzes data acquired by the OCT scan on the three dimensional region to specify a feature position corresponding to a corneal apex.

The twelfth aspect of the exemplary embodiments is the ophthalmic apparatus of the tenth or eleventh aspect, wherein the scan controlling circuitry causes the scanner to perform an OCT scan on a three dimensional region including at least part of a retinal surface of the subject's eye in the second scan control, and the distance calculating circuitry analyzes data acquired by the OCT scan on the three dimensional region to specify a feature position corresponding to a macular center.

The thirteenth aspect of the exemplary embodiments is the ophthalmic apparatus of any one of the first to twelfth aspects, wherein the deviation detector includes: a projection system that projects a light beam onto an anterior eye segment of the subject's eye; two or more cameras that photograph the anterior eye segment from directions different from each other; and deviation calculating circuitry that calculates the deviation of the subject's eye based on positions of images of the light beam in two or more anterior eye segment images acquired by the two or more cameras.

The fourteenth aspect of the exemplary embodiments is the ophthalmic apparatus of any one of the first to twelfth aspects, wherein the deviation detector includes: a projection system that projects a light beam obliquely onto an anterior eye segment of the subject's eye; an image sensor that detects reflection of the light beam from the anterior eye segment; and deviation calculating circuitry that calculates the deviation of the subject's eye based on a position of the reflection detected by the image sensor.

The fifteenth aspect of the exemplary embodiments is a method of controlling an ophthalmic apparatus that includes a scanner configured to apply an optical coherence tomography (OCT) scan to a subject's eye, a movement mechanism configured to move at least part of the scanner, and a deviation detector configured to measure deviation of the subject's eye with respect to a predetermined reference position. The method comprises: a first alignment control step that controls the movement mechanism based on first deviation information of the subject's eye acquired by the deviation detector; a first scan control step that causes the scanner to perform an OCT scan on a first region including a first site of the subject's eye; a second alignment control step that controls the movement mechanism based on second deviation information of the subject's eye acquired by the deviation detector; a second scan control step that causes the scanner to perform an OCT scan on a second region including a second site different from the first site; and a distance calculation step that calculates a distance between the first site and the second site, based on first data acquired by the scanner in the first scan control step and second data acquired by the scanner in the second scan control step.

The sixteenth aspect of the exemplary embodiments is a method of controlling an ophthalmic apparatus that includes a scanner configured to apply an optical coherence tomography (OCT) scan to a subject's eye, and a deviation detector configured to measure deviation of the subject's eye with respect to a predetermined reference position. The method comprises: a first scan control step that causes the scanner to perform an OCT scan on a first region including a first site of the subject's eye; a second scan control step that causes the scanner to perform an OCT scan on a second region including a second site different from the first site; a deviation detection step that causes the deviation detector to perform at least one of acquisition of first deviation information of the subject's eye in response to the first scan control, and acquisition of second deviation information of the subject's eye in response to the second scan control; and a distance calculation step that calculates a distance between the first site and the second site, based on at least one of the first deviation information and the second deviation information acquired in the deviation detection step, first data acquired by the scanner in the first scan control step, and second data acquired by the scanner in the second scan control step.

The seventeenth aspect of the exemplary embodiments is a program that causes a computer to execute the method of the fifteenth or sixteenth aspect.

The eighteenth aspect of the exemplary embodiments is a computer-readable non-transitory recording medium storing the program of the seventeenth aspect.

According to the exemplary embodiments, axial length measurement may be carried out with high reliability regardless of the movement of the subject's eye.

Hereinafter, exemplary aspects of ophthalmic apparatuses, controlling methods thereof, programs, and recording media according to the exemplary embodiments will be described in detail with referring to the drawings. The ophthalmic apparatuses according to the embodiments acquire data by applying an OCT scan to the subject's eye, and determine the distance between two different sites of the subject's eye. Typically, the ophthalmic apparatuses according to the embodiments may sequentially apply OCT scans to the anterior eye segment and the posterior eye segment of the subject's eye, and determine the value of the axial length from the data acquired through the sequential OCT scans.

The following exemplary disclosures describes an ophthalmic apparatus including a combination of spectral domain OCT and a fundus camera; however, embodiments are not limited thereto. The type of OCT employed in embodiments is not limited to spectral domain OCT, and may be swept source OCT, for example.

Spectral domain OCT is an imaging technique performed by splitting light from a low coherence light source into measurement light and reference light, superposing the return light of the measurement light returned from the object with the reference light to generate interference light, detecting the spectral distribution of the interference light using a spectrometer, and applying Fourier transform and other processes to the spectral distribution detected.

Swept source OCT is an imaging technique performed by splitting light emitted from a wavelength tunable light source into measurement light and reference light, superposing the return light of the measurement light returned from the object with the reference light to generate interference light, detecting the interference light by a photodetector such as a balanced photodiode, and applying Fourier transform and other processes to the detected data acquired according to the wavelength sweeping and the measurement light scanning.

As described above, spectral domain OCT is an OCT technique for acquiring a spectral distribution by space division, and swept source OCT is an OCT technique for acquiring a spectral distribution by time division. In addition, the OCT technique utilizable for embodiments is not limited to the two, and embodiments may utilize any type of OCT technique different from them. For example, time domain OCT may be employed.

In the present specification, "image data" and an "image" that is information visualized based thereon may not be distinguished from one another unless otherwise mentioned. Further, a site or tissue of the subject's eye and an image visualizing the site or tissue may not be distinguished from one another unless otherwise mentioned.

First Embodiment

The first embodiment performs an OCT scan (first OCT scan) on the first region of the subject's eye after performing alignment for the subject's eye, performs another OCT scan (second OCT scan) on the second region after performing another alignment, and then calculates the distance between the first site included in the first region and the second site included in the second region based on the first data acquired through the first OCT scan and the second data acquired through the second OCT scan. With this, both the first and second OCT scans can be carried out under appropriate alignment states, thereby making it possible to achieve distance measurement with high reliability even in the case where eye movement occurs between the first and second OCT scans. Some examples of such embodiment are disclosed below.

<Configurations>

The exemplary ophthalmic apparatus 1 shown in FIG. 1 includes the fundus camera unit 2, the OCT unit 100 and the arithmetic and control unit 200. The fundus camera unit 2 is provided with optical systems and mechanisms for acquiring front images of the subject's eye E, and optical systems and mechanisms for performing OCT. The OCT unit 100 includes optical systems and mechanisms for performing OCT. The arithmetic and control unit 200 includes one or more processors configured to execute various processes (e.g., calculations, operations, and controls). In addition to them, the ophthalmic apparatus 1 includes the two anterior eye segment cameras 300 for photographing an anterior eye segment from two directions different from each other.

The fundus camera unit 2 is provided with a chin rest and a forehead rest for supporting the face of the subject. The chin rest and the forehead rest correspond to the supporter 340 shown in FIG. 4A and FIG. 4B. The base 310 stores a drive mechanism and an arithmetic control circuit. The housing 320 provided on the base 310 stores an optical system. The lens container 330 is provided in such a way that it protrudes from the front surface of the housing 320, and accommodates the objective lens 22.

Further, the ophthalmic apparatus 1 includes a lens unit for switching the target of OCT imaging between some sites. More specifically, the ophthalmic apparatus 1 includes the anterior eye segment OCT attachment 400 for applying OCT to an anterior eye segment. For example, the attachment 400 may be configured in the same manner as the optical unit disclosed in Japanese Unexamined Patent Application Publication No. 2015-160103.

As shown in FIG. 1, the attachment 400 can be disposed between the objective lens 22 and the subject's eye E. When the attachment 400 is placed in the optical path, the ophthalmic apparatus 1 can apply an OCT scan to the anterior eye segment. On the other hand, when the attachment 400 is retracted from the optical path, the ophthalmic apparatus 1 can apply an OCT scan to the posterior eye segment. The movement of the attachment 400 is performed manually or automatically.

In another embodiment, an OCT scan may be applied to a posterior eye segment when an attachment is placed in the optical path, and an OCT scan may be applied to an anterior eye segment when the attachment is retracted from the optical path. Further, the target sites switched by the attachment is not limited to the posterior and eye segments, and may be any sites of an eye. Such attachments are not the only configuration of switching the target sites of OCT. For example, the followings may be adopted: a configuration including a lens movable along an optical path; or a configuration including a lens insertable into and removable from an optical path.

In the present embodiment, the term "processor" is, for example, a circuit (circuitry) such as a central processing unit (CPU), a graphics processing unit (GPU), an application specific integrated circuit (ASIC), a programmable logic device (e.g., a simple programmable logic device (SPLD), a complex programmable logic device (CPLD), or a field programmable gate array (FPGA)), or the like. The processor realizes the functions according to the embodiment, for example, by reading out and executing a program stored in a memory circuit or a memory device.

<Fundus Camera Unit 2>

The fundus camera unit 2 is provided with optical systems for photographing the fundus Ef of the subject's eye E. Digital images of the fundus Ef (referred to as fundus images, fundus photographs, or the like) obtained by the fundus camera unit 2 are, in general, front images such as observation images and photographed images. An observation image is obtained by capturing a moving image using near-infrared light. A photographed image is a still image obtained by using flash light in the visible range.

The fundus camera unit 2 includes the illumination optical system 10 and the photography optical system 30. The illumination optical system 10 projects illumination light onto the subject's eye E. The photography optical system 30 detects the return light of the illumination light projected onto the subject's eye E. The measurement light incident from the OCT unit 100 is directed to the subject's eye E through the optical path in the fundus camera unit 2. The return light of the measurement light projected onto the subject's eye E (e.g., the fundus Ef) is directed to the OCT unit 100 through the same optical path in the fundus camera unit 2.

The light output from the observation light source 11 of the illumination optical system 10 (referred to as observation illumination light) is reflected by the concave mirror 12, passes through the condenser lens 13, and becomes near-infrared light after passing through the visible cut filter 14. Further, the observation illumination light is once converged at a location near the photographing light source 15, reflected by the mirror 16, passes through the relay lens system 17, the relay lens 18, the diaphragm 19, and the relay lens system 20, and is directed to the aperture mirror 21. Then, the observation illumination light is reflected on the peripheral part (i.e., the surrounding area of the aperture part) of the aperture mirror 21, penetrates the dichroic mirror 46, and is refracted by the objective lens 22, thereby illuminating the subject's eye E (the fundus Ef thereof). The return light of the observation illumination light from the subject's eye E is refracted by the objective lens 22, penetrates the dichroic mirror 46, passes through the aperture part formed in the center area of the aperture mirror 21, passes through the dichroic mirror 55, travels through the photography focusing lens 31, and is reflected by the mirror 32. Further, the return light passes through the half mirror 33A, is reflected by the dichroic mirror 33, and forms an image on the light receiving surface of the image sensor 35 by the imaging lens 34. The image sensor 35 detects the return light at a predetermined frame rate (capture rate). Note that the focus of the photography optical system 30 can be adjusted to match the fundus Ef or vicinity thereof, and can be adjusted to match the anterior eye segment or vicinity thereof.

The light output from the photographing light source 15 (referred to as photographing illumination light) passes through the same route as that of the observation illumination light and is projected onto the fundus Ef. The return light of the photographing illumination light from the subject's eye E passes through the same route as that of the return light of the observation illumination light, is guided to and passes through the dichroic mirror 33, is reflected by the mirror 36, and forms an image on the light receiving surface of the image sensor 38 by the imaging lens 37.

The liquid crystal display (LCD) 39 displays a fixation target (i.e., a fixation target image). Part of the light beam output from the LCD 39 is reflected by the half mirror 33A, reflected by the mirror 32, travels through the photography focusing lens 31 and the dichroic mirror 55, and passes through the aperture part of the aperture mirror 21. The light beam having passed through the aperture part of the aperture mirror 21 penetrates the dichroic mirror 46, and is refracted by the objective lens 22, thereby being projected onto the fundus Ef. Fixation targets are typically used for guidance and fixation of the line of sight. The direction in which the line of sight of the subject's eye E is guided (and fixed), that is, the direction in which the fixation of the subject's eye E is urged is referred to as a fixation position.

The fixation position can be changed by changing the display position of the fixation target image on the screen of the LCD 39. Examples of fixation positions include a fixation position for acquiring an image centered on the macula, a fixation position for acquiring an image centered on the optic nerve head, a fixation position for acquiring an image centered on a position between the macula and the optic nerve head (i.e., the fundus center position), and a fixation position for acquiring an image of a site far away from the macula (i.e., a peripheral position of the fundus).

A user interface such as a graphical user interface (GUI) for designating at least one of such typical fixation positions can be provided. Further, a user interface such as a GUI for manually changing the fixation position (i.e., the display position of the fixation target) can be provided. In addition, it is also possible to apply a configuration in which the fixation position is automatically set.

The configuration of presenting fixation targets to the subject's eye E for changing fixation positions is not limited to display devices such as LCD. For example, a device that has light emitting elements (e.g., light emitting diodes) disposed in a matrix-like arrangement (referred to as a fixation matrix) can be adopted in place of a display device. In this case, fixation positions of the subject's eye E by the fixation target can be changed by lighting one (or more) of the light emitting elements in a selective manner. As another example, a device provided with one or more movable light emitting elements can generate the fixation target capable of changing fixation positions.

The alignment optical system 50 generates an alignment indicator used for the alignment of the optical system with respect to the subject's eye E. The alignment light output from the light emitting diode (LED) 51 travels through the diaphragm 52, the diaphragm 53, and the relay lens 54, is reflected by the dichroic mirror 55, passes through the aperture part of the aperture mirror 21, penetrates the dichroic mirror 46, and is projected onto the subject's eye E via the objective lens 22. The return light of the alignment light from the subject's eye E passes through the same route as that of the return light of the observation illumination light and is guided to the image sensor 35. Based on the received image (referred to as the alignment indicator image), manual alignment and/or automatic alignment can be performed.

Note that alignment methods applicable to embodiments are not limited to the above method using an alignment indicator. It may be any known method, such as a method using the anterior eye segment camera 300 (described later), or a method using an optical lever configured to project light obliquely onto the cornea and detect the cornea reflection light in the opposite oblique direction (described later).

The focus optical system 60 generates a split indicator used for the focus adjustment with respect to subject's eye E. The focus optical system 60 is moved along the optical path of the illumination optical system 10 (referred to as the illumination optical path) in conjunction with the movement of the photography focusing lens 31 along the optical path of the photography optical system 30 (referred to as the photographing optical path). The reflection rod 67 is inserted into and removed from the illumination optical path. Before performing focus adjustment, the reflective surface of the reflection rod 67 is arranged in the slanted state in the illumination optical path. The focus light output from the LED 61 passes through the relay lens 62, is split into two light beams by the split indicator plate 63, passes through the two-hole diaphragm 64. Then, the focus light is reflected by the mirror 65, is converged on the reflective surface of the reflection rod 67 by the condenser lens 66, and is reflected by the reflective surface. Further, the focus light travels through the relay lens 20, is reflected by the aperture mirror 21, and penetrates the dichroic mirror 46, thereby being projected onto the subject's eye E via the objective lens 22. The return light of the focus light from the subject's eye E (e.g., the fundus reflection light) passes through the same route as that of the return light of the alignment light and is guided to the image sensor 35. Based on the received image (referred to as the split indicator image), manual focusing and/or automatic focusing can be performed.

The diopter correction lenses 70 and 71 can be selectively inserted into the photographing optical path between the aperture mirror 21 and the dichroic mirror 55. The diopter correction lens 70 is a positive lens (convex lens) for correcting high hyperopia. The diopter correction lens 71 is a negative lens (concave lens) for correcting high myopia.

The dichroic mirror 46 couples the optical path for fundus photography and the optical path for OCT (measurement arm). The dichroic mirror 46 reflects the light of wavelength bands used for OCT and transmits the light for fundus photography. The measurement arm is formed by, listed from the OCT unit 100 side, the collimator lens unit 40, the retroreflector 41, the dispersion compensation member 42, the OCT focusing lens 43, the optical scanner 44, and the relay lens 45.

The retroreflector 41 is movable along the optical path of the measurement light LS incident on the retroreflector 41, whereby the length of the measurement arm is changed. The change in the length of the measurement arm can be utilized for operations such as optical path length correction according to axial length and interference condition adjustment.

The dispersion compensation member 42 acts to eliminate the difference between the dispersion characteristics of the measurement light LS and that of the reference light LR, together with the dispersion compensation member 113 (described later) arranged in the reference arm.

The OCT focusing lens 43 is moved along the measurement arm in order to perform the focus adjustment of the measurement arm. Note that the movements of the photography focusing lens 31, the focus optical system 60 and the OCT focusing lens 43 may be controlled in an interlocking manner.

The optical scanner 44 is placed at a position substantially optically conjugate with the pupil of the subject's eye E. The optical scanner 44 is configured to deflect the measurement light LS guided by the measurement arm. An example of the optical scanner 44 is a galvano scanner that allows two dimensional scanning. Typically, the optical scanner 44 includes a one dimensional scanner for deflecting the measurement light in the +x and −x directions (x-scanner), and another one dimensional scanner for deflecting the measurement light in the +y and −y directions (y-scanner). In this case, for example, either one of the one dimensional scanners may be placed at a position optically conjugate with the pupil, or a position optically conjugate with the pupil is placed between the one dimensional scanners.

<OCT Unit 100>

Figure 2:
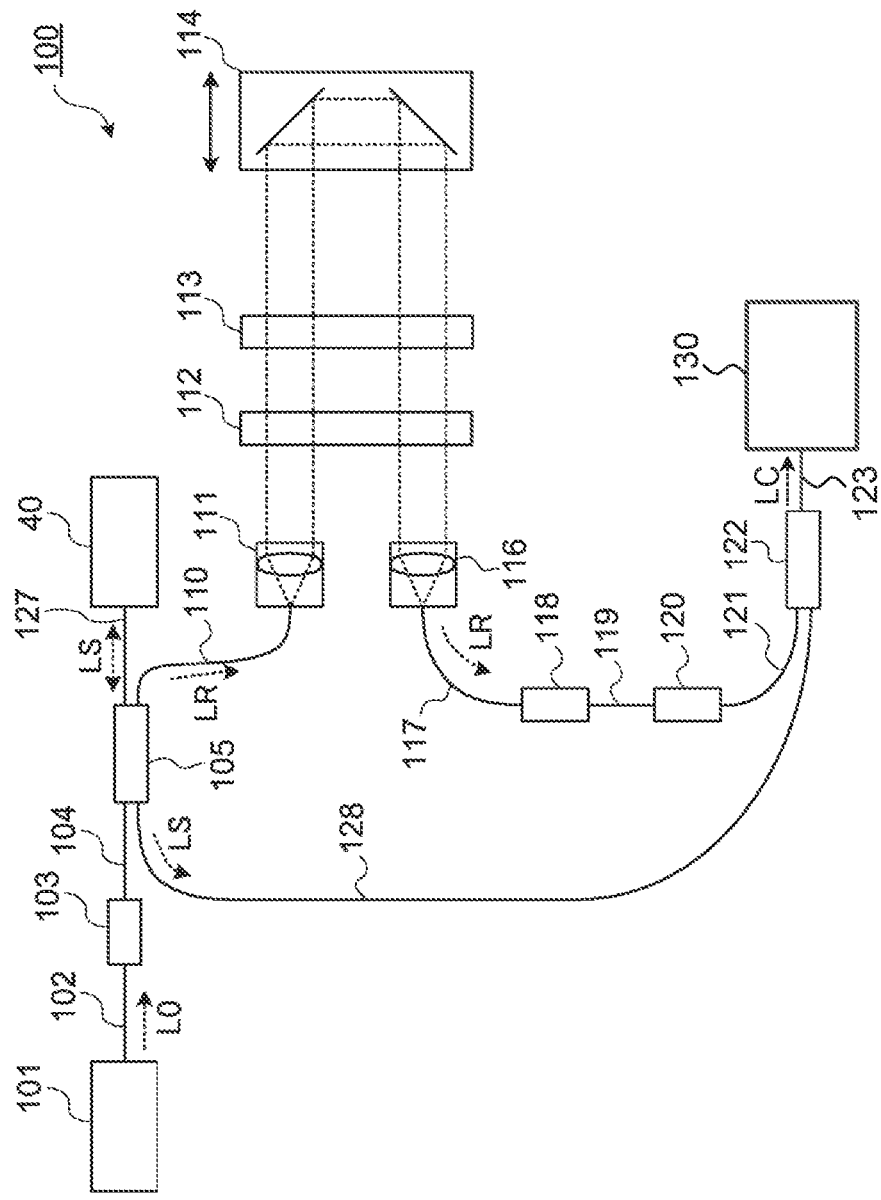
FIG. 2 is a schematic diagram illustrating an example of the configuration of the ophthalmic apparatus according to the exemplary embodiment.

The exemplary OCT unit 100 shown in FIG. 2 is provided with the optical system for performing spectral domain OCT. The optical system includes an interference optical system. The interference optical system is configured to split light emitted from a wavelength tunable light source into measurement light and reference light, superpose the return light of the measurement light projected onto the subject's eye E with the reference light having traveled through the reference optical path, thereby yielding interference light. The spectral distribution of the interference light generated by the interference optical system is detected with a spectrometer. The data (i.e., a detection signal) obtained by detecting the spectral distribution of the interference light is sent to the arithmetic and control unit 200.

The light source unit 101 outputs the low coherence light L0 (broadband low coherence light). The low coherence light L0 includes, for example, wavelength bands in the near-infrared region (about 800 nm to 900 nm), and has a temporal coherence length of about several tens of micrometers. The low coherence light L0 may be invisible to human eyes, such as near-infrared light having a central wavelength of about 1040 nm to 1060 nm. The light source unit 101 includes a light output device such as a super luminescent diode (SLD), LED, semiconductor optical amplifier (SOA), or the like.

In the case where swept source OCT is employed in place of spectral domain OCT, a light source unit is used that includes a near-infrared wavelength tunable laser configured to vary wavelengths of emitted light at high speed.

The low coherence light L0 output from the light source unit 101 is guided to the polarization controller 103 through the optical fiber 102, and the polarization state of the light L0 is regulated. The light L0 with regulated polarization state is guided to the fiber coupler 105 through the optical fiber 104 and is split into the measurement light LS and the reference light LR. The optical path guiding the measurement light LS is referred to as a measurement arm (or a sample arm), and the optical path guiding the reference light LR is referred to as a reference arm.

The reference light LR generated by the fiber coupler 105 is guided through the optical fiber 110 to the collimator 111, is converted into a parallel light beam, travels through the optical path length correction member 112 and the dispersion compensation member 113, and is guided to the retroreflector 114. The optical path length correction member 112 acts to match the optical path length of the reference light LR and that of the measurement light LS with each other. The dispersion compensation member 113 acts to eliminate the difference between the dispersion characteristics of the reference light LR and that of the measurement light LS with each other, together with the dispersion compensation member 42 arranged in the measurement arm. The retroreflector 114 is movable along the optical path of the reference light LR incident on the retroreflector 114. With this, the length of the reference arm is changed. The change in the length of the reference arm may be utilized for operations such as optical path length correction according to axial length and interference condition adjustment.

After passing through the retroreflector 114, the reference light LR travels through the dispersion compensation member 113 and the optical path length correction member 112, is converted from a parallel light beam to a convergent light beam by the collimator 116, and is incident on the optical fiber 117. The reference light LR having entered the optical fiber 117 is guided to the polarization controller 118, and the polarization state of the reference light LR is regulated. Then, the reference light LR is guided to the attenuator 120 through the optical fiber 119, and the light amount of the reference light LR is regulated. Subsequently, the reference light LR is guided to the fiber coupler 122 through the optical fiber 121.

Meanwhile, the measurement light LS generated by the fiber coupler 105 is guided to the collimator lens unit 40 through the optical fiber 127 and is converted to a parallel light beam. Then, the measurement light LS passes through the retroreflector 41, the dispersion compensation member 42, the OCT focusing lens 43, the optical scanner 44, and the relay lens 45, and then reaches the dichroic mirror 46. The measurement light LS is reflected by the dichroic mirror 46, is refracted by the objective lens 22, and is projected onto the subject's eye E. The measurement light LS is reflected and scattered at various depths of the subject's eye E. The return light of the measurement light LS returned from the subject's eye E travels along the measurement arm in the opposite direction, is directed to the fiber coupler 105, and then reaches the fiber coupler 122 via the optical fiber 128.

The fiber coupler 122 superposes the measurement light LS incident through the optical fiber 128 with the reference light LR incident through the optical fiber 121, to generate the interference light LC.

The interference light LC generated by the fiber coupler 122 is guided to the spectrometer 130 through the optical fiber 129. For example, the spectrometer 130 is configured to convert the incident interference light LC into a parallel light beam by a collimator lens, separate the interference light LC (parallel light beam) into its constituent wavelength components by a diffraction grating, and project the spectral components onto an image sensor by the lens 114. The image sensor is, for example, a line sensor that detects the spectral components of the interference light LC to generate an electrical signal (i.e., detection signal). The detection signal generated is sent to the arithmetic and control unit 200.

When swept source OCT is employed, interference light generated by superposition of measurement light and reference light is split at a predetermined splitting ratio (e.g., 1 to 1) to generate a pair of interference light. The pair of interference light is guided to a photodetector. The photodetector includes, for example, a balanced photodiode that includes a pair of photodiodes configured to respectively detect the pair of interference light and output the difference between the pair of detection signals obtained by the pair of photodiodes. The photodetector transmits the output (i.e., detection signal such as the difference signal) to a data acquisition system (DAQ). A clock signal is supplied from the light source unit to the data acquisition system. The clock signal is generated in the light source unit in synchronization with the output timings of the respective wavelengths varied within a predetermined wavelength range by the wavelength tunable type light source. For example, the light source unit splits light of each output wavelength to generate two pieces of split light, optically delays one of the two pieces of split light, combines the two pieces of split light, detects the combined light, and generates a clock signal from the detection signal thereof. The data acquisition system performs sampling of the detection signal (difference signal) input from the photodetector based on the clock signal. The data extracted by the sampling is used for processing such as image construction.

The ophthalmic apparatus 1 shown in FIG. 1 and FIG. 2 is provided with both an element for changing the measurement arm length (e.g., the retroreflector 41) and an element for changing the reference arm length (e.g., the retroreflector 114 or a reference mirror); however, only one of these two elements may be provided in some other embodiments. The coherence gate position is changed by changing the difference between the measurement arm length and the reference arm length (i.e., the optical path length difference). Elements for changing the optical path length difference are not limited to the exemplary elements in the present embodiment, and any type of element (e.g., any type of optical member, any type of mechanism) may be employed.

<Arithmetic and Control Unit 200>

The arithmetic and control unit 200 controls each part of the ophthalmic apparatus 1. Further, the arithmetic and control unit 200 executes various kinds of arithmetic processes. For example, the arithmetic and control unit 200 applies signal processing such as Fourier transform on the spectral distribution acquired by the spectrometer 130, to create reflection intensity profiles respectively for A-lines. Furthermore, the arithmetic and control unit 200 applies imaging processing to the reflection intensity profiles for the A-lines to construct image data. Arithmetic processes for the image data construction are the same as those of conventional spectral domain OCT.

The arithmetic and control unit 200 includes, for example, a processor, random access memory (RAM), read only memory (ROM), hard disk drive, and communication interface. A storage device such the hard disk drive stores various kinds of computer programs. The arithmetic and control unit 200 may include an operation device, input device, display device, etc.

<User Interface 240>

The user interface 240 includes the display device 241 and the operation device 242. The display device 241 includes the display device 3. The operation device 242 includes various kinds of operation devices and input devices. The user interface 240 may include a device having both display and operation functions, such as a touch panel display. Some embodiments may be configured not to include at least part of the user interface 240. For example, the display device may be an external device connected to the ophthalmic apparatus.

<Anterior Eye Segment Cameras 300>

Figure 4A:
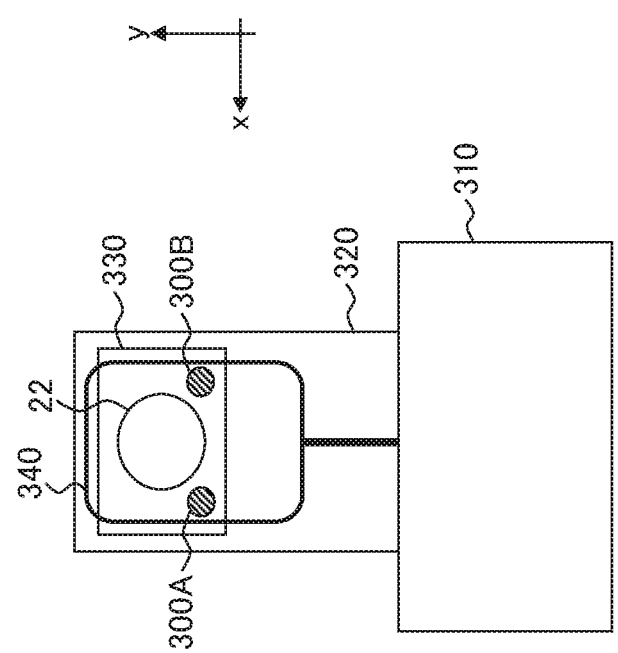
FIG. 4A is a schematic diagram illustrating an example of the configuration of the ophthalmic apparatus according to the exemplary embodiment.
Figure 4B:
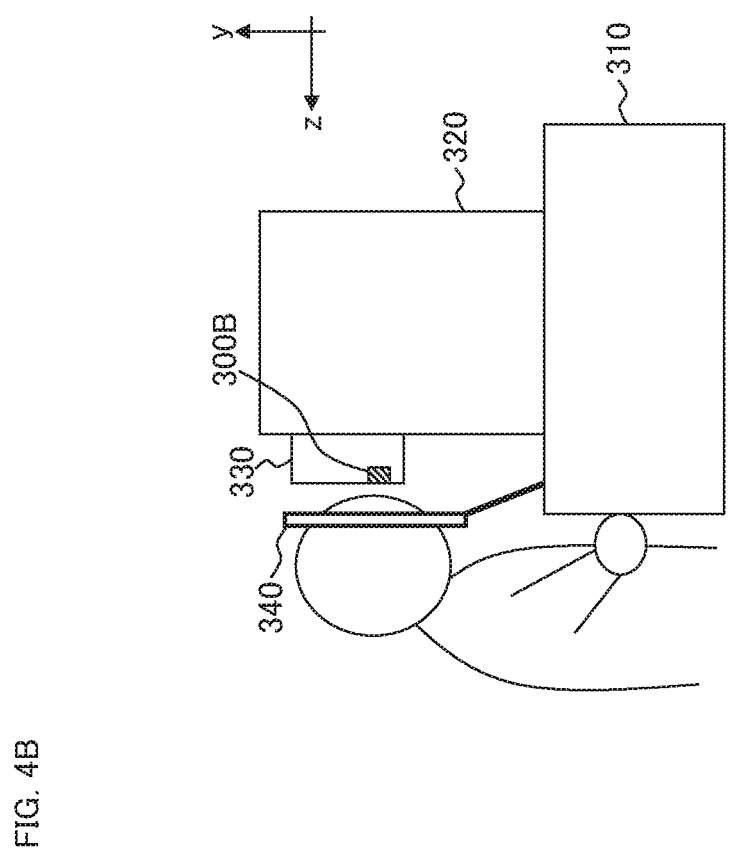
FIG. 4B is a schematic diagram illustrating an example of the configuration of the ophthalmic apparatus according to the exemplary embodiment.

The anterior eye segment cameras 300 photograph the anterior eye segment of the subject's eye E from two or more different directions. The anterior eye segment camera 300 includes an imaging element such as a CCD image sensor or CMOS image sensor. The present embodiment includes the two anterior eye segment cameras 300 placed on the surface of the fundus camera unit 2 on the subject side (see the anterior eye segment cameras 300A and 300B illustrated in FIG. 4A). As shown in FIG. 1 and FIG. 4A, the anterior eye segment cameras 300A and 300B are placed in positions outside the optical path that passes through the objective lens 22. Hereinafter, any one or both of the anterior eye segment cameras 300A and 300B may be denoted by the reference symbol "300". In addition, anterior eye segment cameras that can be adopted instead of the anterior eye segment cameras 300A and 300B may be denoted by the reference symbol "300".

Although the two anterior eye segment cameras 300A and 300B are provided in the present embodiment, the number of the anterior eye segment cameras 300 may be any number of two or more. In consideration of the calculation processing described later, it is sufficient to employ (but not limited to) a configuration capable of photographing the anterior eye segment from two different directions. Alternatively, one or more movable anterior eye segment camera 300 may be provided to sequentially perform two or more times of anterior eye segment photography at two or more different positions.

The present embodiment is provided with the anterior eye segment cameras 300 separately from the illumination optical system 10 and the photography optical system 30. However, for example, the photography optical system 30 can be used for anterior eye segment photography. In other words, one of the two or more anterior eye segment cameras 300 may be the photography optical system 30. The anterior eye segment cameras 300 of the present embodiment may be capable of photographing the anterior eye segment from two (or more) directions different from each other.

A configuration for illuminating the anterior eye segment may be provided. The anterior eye segment illuminating means may include one or more light sources. Typically, at least one light source (e.g., infrared light source(s)) may be provided in the vicinity of each of the two or more anterior eye segment cameras 300.

In the case where the two or more anterior eye segment cameras 300 are provided, the anterior eye segment may be photographed substantially simultaneously from two or more different directions. The substantially simultaneous photography here means that the case where the photography timings by the two or more anterior eye segment cameras are simultaneous. In addition, this also means to tolerate, for example, a negligible time lag in photography with respect to eye movement. Such substantially simultaneous photography enables the two or more anterior eye segment cameras to capture two or more images of the subject's eye E in substantially the same position and orientation.

The photography with two or more anterior eye segment cameras may be motion-picture photography or still-picture photography. In the case of motion-picture photography, the substantially simultaneous anterior eye segment photography described above can be achieved by matching photography start timings of the two or more anterior eye segment cameras, or by controlling frame rates and/or frame capture timings thereof. On the other hand, in the case of still-picture photography, substantially simultaneous anterior eye segment photography can be achieved by controlling capture timings of the two or more anterior eye segment cameras.

<Control System>

Figure 3A:
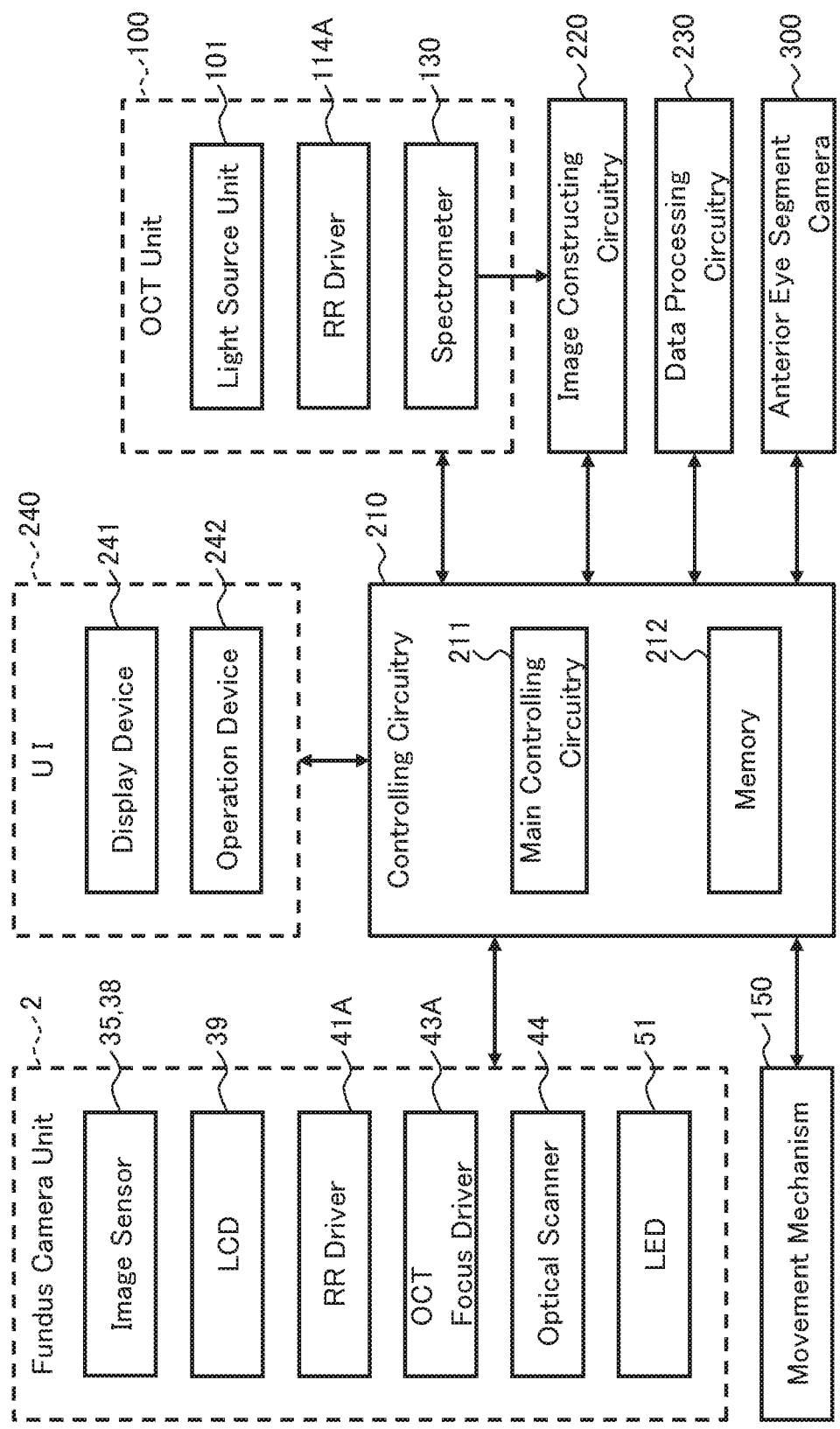
FIG. 3A is a schematic diagram illustrating an example of the configuration of the ophthalmic apparatus according to the exemplary embodiment.
Figure 3B:
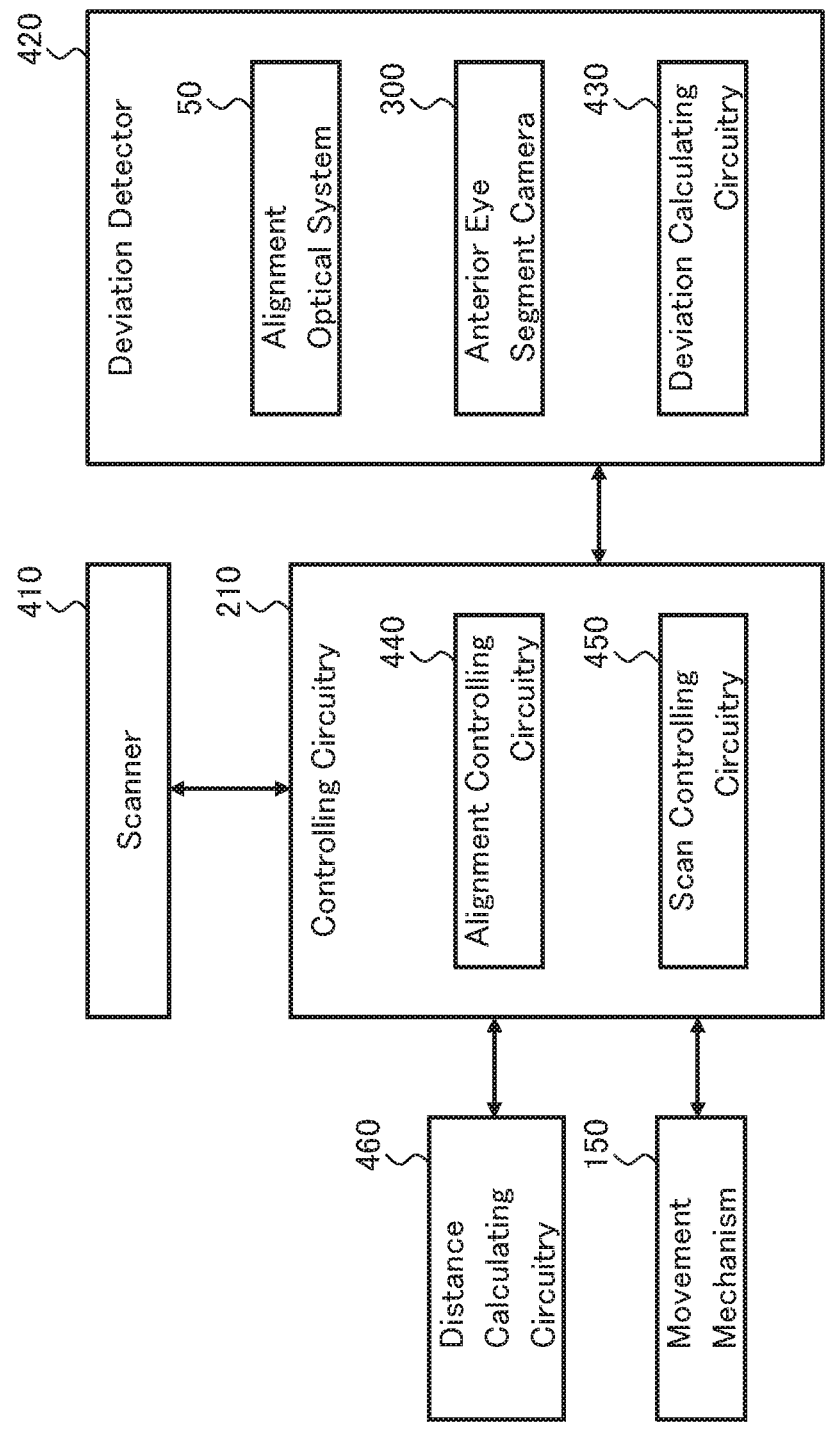
FIG. 3B is a schematic diagram illustrating an example of the configuration of the ophthalmic apparatus according to the exemplary embodiment.

FIG. 3A and FIG. 3B show an example of the configuration of the control system (processing system) of the ophthalmic apparatus 1. The controlling circuitry 210, the image constructing circuitry 220 and the data processing circuitry 230 are provided, for example, in the arithmetic and control unit 200.

<Controlling Circuitry 210>

The controlling circuitry 210 includes a processor and controls each part of the ophthalmic apparatus 1. The controlling circuitry 210 includes the main controlling circuitry 211 and the memory 212.

<Main Controlling Circuitry 211>

The main controlling circuitry 211 includes a processor, and controls each element of the ophthalmic apparatus 1 (including the elements shown in FIG. 1 to FIG. 3B). The main controlling circuitry 211 is realized by the cooperation of hardware including a circuit (circuitry) and controlling software.

The photography focusing lens 31 disposed in the photography optical path and the focus optical system 60 disposed in the illumination optical path are moved in an integral or interlocking manner by a photography focus driver (not shown) under control of the main controlling circuitry 211. The retroreflector 41 disposed in the measurement arm is moved by the retroreflector driver (RR driver) 41A under control of the main controlling circuitry 211. The OCT focusing lens 43 disposed in the measurement arm is moved by the OCT focus driver 43A under control of the main controlling circuitry 211. Note that the movement of the OCT focusing lens 43 can be performed in an interlocking manner with the movement of the photography focusing lens 31 and the focus optical system 60. The retroreflector 114 disposed in the reference arm is moved by the retroreflector driver (RR driver) 114A under control of the main controlling circuitry 211. Each of the mechanisms exemplified here typically includes an actuator such as a pulse motor that operates under control of the main controlling circuitry 211. The optical scanner 44 disposed in the measurement arm operates under control of the main controlling circuitry 211. Further, the main controlling circuitry 211 can control any of the elements included in the ophthalmic apparatus 1 such as the polarization controller 103, the polarization controller 118, the attenuator 120, various kinds of light sources, various kinds of optical elements, various kinds of devices, and various kinds of mechanisms. Also, the main controlling circuitry 211 may be configured to execute control of any peripheral device (apparatus, equipment, instrument, device, etc.) connected to the ophthalmic apparatus 1, and/or control of any apparatus, equipment, instrument, device, etc. accessible by the ophthalmic apparatus 1.

The movement mechanism 150 moves, for example, at least the fundus camera unit 2 in a three dimensional manner. In a typical example, the movement mechanism 150 includes the followings: an x stage movable in the +x and −x directions (i.e., left and right directions); an x movement mechanism that moves the x stage; a y stage movable in the +y and −y directions (i.e., up and down directions); a y movement mechanism that moves the y stage; a z stage movable in the +z and -z directions (i.e., depth direction); and a z movement mechanism that moves the z stage. Each of the movement mechanisms described here includes an actuator such as a pulse motor that operates under control of the main controlling circuitry 211.

<Memory 212>

The memory 212 stores various kinds of data. Examples of the data stored in the memory 212 include image data of OCT images, image data of fundus images, and subject's eye information. The subject's eye information includes subject information such as patient IDs and patient's names, identification information for the left eye and the right eye, and electronic medical record information.

<Image Constructing Circuitry 220>

The image constructing circuitry 220 constructs OCT image data based on data acquired by the spectrometer 130. The image constructing circuitry 220 includes a processor. The image constructing circuitry 220 is realized by the cooperation of hardware including a circuit (circuitry) and image constructing software.

The image constructing circuitry 220 constructs cross sectional image data based on data acquired by the spectrometer 130. The image constructing processing includes signal processing such as sampling (A/D conversion), noise elimination (noise reduction), filtering, fast Fourier transform (FFT), and other processes as in conventional spectral domain OCT.

Image data constructed by the image constructing circuitry 220 is a data set including a group of a plurality of pieces of image data (a group of a plurality of pieces of A-scan image data or an A-scan image data group) constructed by applying imaging processing to reflection intensity profiles at corresponding A-lines arranged in the area to which OCT scans are applied. An A-line is a scan line lying along the z direction.

Image data constructed by the image constructing circuitry 220 is, for example, B-scan image data or stack data. Stack data is constructed by embedding a plurality of pieces of B-scan image data in a single three dimensional coordinate system. The image constructing circuitry 220 may apply voxelization processing to stack data to construct volume data (voxel data). Stack data and volume data are typical examples of three dimensional image data. Three dimensional image data is image data that is represented by a three dimensional coordinate system.

The image constructing circuitry 220 may be configured to apply image processing to three dimensional image data. For example, the image constructing circuitry 220 may construct new image data by applying rendering to three dimensional image data. Examples of the rendering method include volume rendering, maximum intensity projection (MIP), minimum intensity projection (MinIP), surface rendering, and multi planar reconstruction (MPR). Further, the image constructing circuitry 220 may be configured to construct projection data by projecting three dimensional image data in the z direction (i.e., the A-line direction or the depth direction). In addition, the image constructing circuitry 220 may be configured to construct a shadowgram by projecting part of three dimensional image data (i.e., three dimensional partial image data) in the z direction. Three dimensional partial image data is designated, for example, by applying segmentation to three dimensional image data.

<Data Processing Circuitry 230>

The data processing circuitry 230 performs various kinds of data processing. For example, the data processing circuitry 230 may be configured to apply image processing and/or analysis processing to OCT image data, and/or, apply image processing and/or analysis processing to observation image data and/or photographed image data. The data processing circuitry 230 includes, for example, at least one of a processor and a dedicated circuit board. The data processing circuitry 230 is realized by the cooperation of hardware including a circuit (circuitry) and data processing software.

Next, the functional configuration of the ophthalmic apparatus 1 realized by the elements (hardware elements, software elements) shown in FIG. 1 to FIG. 3A will be described. FIG. 3B shows an example of the functional configuration of the ophthalmic apparatus 1. Note that, of the elements shown in FIG. 3B, the same elements as in FIG. 3A are indicated by the same reference symbols.

<Scanner 410>

The scanner 410 applies OCT scans to the subject's eye E to acquire data. The data acquired by the scanner 410 may be any kind of data from among, for example, the first data acquired by the spectrometer 130, the second data generated by the image constructing circuitry 220 from the first data (e.g., sampling data, reflection intensity profile, or image data), and data generated by the data processing circuitry 230 from the second data (e.g., image data). As such, the scanner 410 include at least the spectrometer 130, may further include at least part of the image constructing circuitry 220, and may still further include at least part of the data processing circuitry 230.

The scanner 410 includes an interference optical system including the measurement arm that guides the measurement light LS to the subject's eye E and the reference arm that guides the reference light LR. As described above, the measurement arm is provided with the OCT focusing lens 43, the optical scanner 44, etc., and the reference arm is provided with the polarization controller 118, the attenuator 120, etc. The interference optical system includes the spectrometer 130.

Further, the scanner 410 includes an arm length changer provided in at least one of the measurement arm and the reference arm. The arm length changer includes any one or both of the combination of the retroreflector 41 and the retroreflector driver 41A and the combination of the retroreflector 114 and the retroreflector driver 114A. The arm length changer changes the arm length under the control of the scan controlling circuitry 450 described later. More specifically, in the case where the arm length changer includes the combination of the retroreflector 41 and the retroreflector driver 41A, the arm length changer can change the measurement arm length. In the case where the arm length changer includes the combination of the retroreflector 114 and the retroreflector driver 114A, the arm length changer can change the reference arm length.

<Deviation Detector 420>

The deviation detector 420 measures the deviation (or positional error) of the subject's eye E with respect to a reference position set in advance. The alignment controlling circuitry 440, which will be described later, performs alignment control based on the measurement result of the deviation (deviation information) acquired by the deviation detector 420. The alignment control includes control of the movement mechanism 150 on the basis of the deviation information. For example, the alignment control is a process of moving the optical system to cancel (eliminate) the deviation obtained by the deviation detector 420. The optical system moved includes at least the measurement arm.

The deviation of the subject's eye E from the reference position is a relative position with respect to the reference position, and is typically a vector quantity that possesses both magnitude and direction.

The reference position may be set based on, for example, the optical system configuration of the ophthalmic apparatus 1. The reference position typically includes a reference position in the x direction, a reference position in the y direction, and a reference position in the z direction. In other words, the reference position is typically a three dimensional position. The reference position is not limited to such a three dimensional position, and may be a two dimensional position or a one dimensional position.

As described above, the deviation of the subject's eye E with respect to the reference position is a relative position. Therefore, in the case where the reference position is set based on the optical system configuration of the ophthalmic apparatus 1, the deviation of the subject's eye E with respect to the optical system of the ophthalmic apparatus 1 and the deviation of the optical system with respect to the subject's eye E are identical with each other. Even in the event that the reference position is not set based on the optical system of the ophthalmic apparatus 1, the deviation of the subject's eye E with respect to the optical system of the ophthalmic apparatus 1 and the deviation with respect to the optical system with respect to the subject's eye E are identical with each other for that reference position.

The combination of the reference position in the x direction and the reference position in the y direction (xy reference position) is, for example, the position of the optical axis of the ophthalmic apparatus 1 (optical axis position). The optical axis position may be the position of the optical axis of the objective lens 22. If this is the case, the deviation detector 420 may be configured to determine the deviation of subject's eye E with respect to the optical axis position in the xy plane (i.e., the xy coordinate system).

On the other hand, the reference position in the z direction (z reference position) is, for example, a position distant from the optical system (front surface of the objective lens 22) of the ophthalmic apparatus 1 by a predetermined distance in the +z direction. In such a case, the deviation detector 420 may be configured to determine the deviation of the subject's eye E with respect to the z reference position in the z direction (i.e., the z coordinate).

The predetermined distance in the definition of the z reference position is, for example, a working distance set in advance or a distance obtained by adding a predetermined value to the working distance. Examples of the predetermined value include a half value of corneal curvature radius and the distance between cornea and pupil.

In the case where alignment is performed using the corneal surface as a reference, the working distance may be adopted to be the predetermined distance. In the case where alignment is performed using the bright spot (Purkinje image) formed on the anterior eye segment as a reference the distance obtained by adding a half value of the corneal curvature radius to the working distance may be adopted to be the predetermined distance. In the case where alignment is performed using the pupil as a reference, the distance obtained by adding the value of the cornea-pupil distance to the working distance may be adopted to be the predetermined distance. Note that the corneal curvature radius and the cornea-pupil distance may be the values obtained by actual measurement of the subject's eye E.

An example of the three dimensional reference position is a position distant from the front surface of the objective lens 22 by the predetermined distance in the +z direction on the optical axis of the ophthalmic apparatus 1.

It is necessary to define the position of the subject's eye E in order to obtain the deviation of the subject's eye E with respect to the reference position. The position of the subject's eye E is defined, for example, to be the position of the bright spot formed on the anterior eye segment, the position of the pupil center (the position of the center of gravity of the pupil), or the position of the corneal apex.

In the case where the position of the subject's eye E is defined to be the bright spot position, the deviation detector 420 may be configured to specify the bright spot positions from two anterior eye segment images acquired by the two anterior eye segment cameras 300, and determine the deviation of the subject's eye E with respect to the reference position. The processes of this example may be carried out, for example, in accordance with the processing method disclosed in Japanese Unexamined Patent Application Publication No. 2017-074115 and Japanese Unexamined Patent Application Publication No. 2017-225638 filed by the present applicant.

In the case where the position of the subject's eye E is defined to be the pupil center position, the deviation detector 420 may be configured to specify the pupil center positions from two anterior eye segment images acquired by the two anterior eye segment cameras 300, and determine the deviation of the subject's eye E with respect to the reference position. The processes of this example may be carried out, for example, in accordance with the processing method disclosed in Japanese Unexamined Patent Application Publication No. 2013-248376 and Japanese Unexamined Patent Application Publication No. 2017-225638 filed by the present applicant.

In the case where the position of the subject's eye E is defined to be the corneal apex position, the deviation detector 420 may be configured to specify the corneal apex positions from two anterior eye segment images acquired by the two anterior eye segment cameras 300, and determine the deviation of the subject's eye E with respect to the reference position. The processes of this example may be carried out, for example, in accordance with the processing method disclosed in Japanese Unexamined Patent Application Publication No. 2017-225638 filed by the present applicant.

Note that the definition of the reference position, the definition of the position of the subject's eye E, the processing method for specifying the position of the subject's eye E, and the method of calculating the deviation of the subject's eye E with respect to the reference position are not limited to the examples described above and may be arbitrary. For example, an alignment method based on the positional relationship between two bright spots, or an alignment method using an optical lever may be employed.

The deviation detector 420 shown in FIG. 3B is an example applicable to the case where the position of the subject's eye E is defined to be the bright spot position. The deviation detector 420 in the present example includes the alignment optical system 50, the two anterior eye segment cameras 300, and the deviation calculating circuitry 430. The deviation calculating circuitry 430 is included in the data processing circuitry 230, and is realized by the cooperation of hardware including a circuit (circuitry) and deviation calculating software.

As described above, the alignment optical system 50 projects the alignment indicator onto the anterior eye segment of the subject's eye E. In other words, the alignment optical system 50 corresponds to a projection system configured to project a light beam onto the anterior eye segment of the subject's eye E.

The two anterior eye segment cameras 300 photograph the anterior eye segment of the subject's eye E from different directions during the light beam is being projected by the alignment optical system 50. With this, two anterior eye segment images corresponding to directions different from each other can be obtained. In each of the anterior eye segment images, the image of the light beam projected by the alignment optical system 50 is depicted. That is, the bright spot used as the alignment indicator is depicted.

The deviation calculating circuitry 430 calculates the deviation of the subject's eye E with respect to the predetermined reference position based on the positions of the two bright spots rendered respectively in the two anterior eye segment images acquired by the two anterior eye segment cameras 300.

The deviation calculating circuitry 430 analyzes each of the two anterior eye segment images to detect bright spots, and specifies the position of the subject's eye E based on the two bright spots detected from the two anterior eye segment images. The processes of this example may be carried out in a similar manner to the processing method disclosed in Japanese Unexamined Patent Application Publication No. 2017-074115 and Japanese Unexamined Patent Application Publication No. 2017-225638.

For example, the deviation calculating circuitry 430 may calculate the distance between the subject's eye E and the ophthalmic apparatus 1 (e.g., the objective lens 22) in the direction along the optical axis of the ophthalmic apparatus 1 (i.e., the z direction), based on the relative position of the two bright spots detected from the two anterior eye segment images. Based on the distance calculated, the alignment controlling circuitry 440 may control the movement mechanism 150 in such a way that the distance between the subject's eye E and the ophthalmic apparatus 1 in the z direction coincides with the working distance.

Further, based on the positions of the two bright spots detected from the two anterior eye segment images, the deviation calculating circuitry 430 may calculate the deviation between the subject's eye E and the ophthalmic apparatus 1 in the direction orthogonal to the z direction (i.e., the x and y directions). Based on the deviation calculated, the alignment controlling circuitry 440 may control the movement mechanism 150 in such a way that the optical axis of the ophthalmic apparatus 1 coincides with the axis of the subject's eye E.

In addition, in the event that no bright point is detected from any one or both of the two anterior eye segment images, another alignment method (e.g., alignment on the basis of pupil center) may be employed.

The ophthalmic apparatus 1 performs the first OCT scan and the second OCT scan. The first OCT scan is performed on the first region including the first site of the subject's eye E. The first region is, for example, the anterior eye segment region, and the first site is, for example, the corneal surface. The second OCT scan is performed on the second region including the second site. The second region is, for example, the posterior eye segment region, and the second site is, for example, the retinal surface. Details of the first and second OCT scans will be described later. The deviation detector 420 performs the first deviation measurement prior to the first OCT scan to acquire the first deviation information, and further performs the second deviation measurement prior to the second OCT scan to acquire the second deviation information. Typically, the first deviation measurement is performed immediately before the first OCT scan, and the second deviation measurement is performed immediately before the second OCT scan.

The execution order of the first OCT scan and the second OCT scan is arbitrary. The second OCT scan may be performed after the first OCT scan, or the first OCT scan may be performed after the second OCT scan.

<Alignment Controlling Circuitry 440>

The alignment controlling circuitry 440 performs the first alignment control and the second alignment control. The first alignment control is executed to control the movement mechanism 150 based on the first deviation information acquired by the deviation detector 420 prior to the first OCT scan. The second alignment control is executed to control the movement mechanism 150 based on the second deviation information acquired by the deviation detector 420 prior to the second OCT scan.

For example, in the same manner as the alignment method disclosed in any one of Japanese Unexamined Patent Application Publication No. 2017-074115, Japanese Unexamined Patent Application Publication No. 2017-225638, and Japanese Unexamined Patent Application Publication No. 2013-248376, the alignment controlling circuitry 440 performs the first alignment control so as to cancel out the deviation indicated by the first deviation information, and also performs the second alignment control so as to cancel out the deviation indicated by the second deviation information.

The alignment controlling circuitry 440 is included in the controlling circuitry 210, and is realized by the cooperation of hardware including a circuit (circuitry) and alignment controlling software.

<Scan Controlling Circuitry 450>

The scan controlling circuitry 450 performs control for the first and second OCT scans described above. More specifically, the scan controlling circuitry 450 performs the followings: the first scan control for causing the scanner 410 to perform the first OCT scan on the first region (e.g., the anterior eye segment region) including the first site (e.g., the corneal surface) of the subject's eye E; and the second scan control for causing the scanner 410 to perform the second OCT scan on the second region (e.g., the posterior eye segment region) including the second site (e.g., the retinal surface).

Each of the first scan control and the second scan control includes, for example, control of the arm length changer (any one or both of the retroreflector driver 41A and the retroreflector driver 114A), control of the light source unit 101, and control of the optical scanner 44. Note that each of the first scan control and the second scan control may further include any of the followings: control of the polarization controller 103; control of the polarization controller 118; control of the attenuator 120; and control of the OCT focus driver 43A. Examples of the first scan control and the second scan control will be described later.

The scan controlling circuitry 450 is included in the controlling circuitry 210, and is realized by the cooperation of hardware including a circuit (circuitry) and scan controlling software.

<Distance Calculating Circuitry 460>

The distance calculating circuitry 460 calculates the distance between the first site included in the target area of the first OCT scan and the second site included in the target area of the second OCT scan, based on the first data acquired by the first OCT scan and the second data acquired by the second OCT scan. In other words, the distance calculating circuitry 460 calculates the distance between the first site and the second site of the subject's eye E, based on the first data acquired by the scanner 410 under the first scan control and the second data acquired by the scanner 410 under the second scan control.

For example, in the case where the first site is the corneal surface and the second site is the retinal surface, that is, in the case where the first OCT scan is applied to the anterior eye segment region including (at least part of) the corneal surface, and where the second OCT scan is applied to the posterior eye segment region including (at least part of) the retinal surface, the distance calculating circuitry 460 may calculate the distance between the corneal surface and the retinal surface. Typically, the distance calculating circuitry 460 may calculate the axial length indicating the distance between the corneal apex and the macular center (fovea centralis).

For example, the distance calculating circuitry 460 performs the distance calculation by a series of processes (first to fourth processes) shown below. Here, the execution order of the first to third processes is arbitrary, and any two or more of these processes may be performed in parallel.

In the first process, the distance calculating circuitry 460 calculates the difference between the first arm length applied at the time of the first scan control, and the second arm length applied at the time of the second scan control. The first arm length and the second arm length are obtained, for example, from the scan controlling circuitry 450 that has performed the first scan control and the second scan control. Alternatively, any one or both of the first arm length and the second arm length may be detected with a means of detecting the arm length. The arm length detecting means is, for example, a position sensor configured to detect any one or both of the position of the retroreflector 41 and that of the retroreflector 114.

In the second process, the distance calculating circuitry 460 analyzes the first data acquired by the scanner 410 under the first scan control, to specify a position (first position) in the first data corresponding to the first site of the subject's eye E. For example, in the case where the first site is the corneal surface, the distance calculating circuitry 460 analyzes the first data acquired by applying the first OCT scan to the anterior eye segment region, to specify the first position corresponding to the corneal surface of the subject's eye E (typically the corneal apex). Typically, the first position is a signal position in the reflection intensity profile generated from the detection signal acquired in the first OCT scan, or a pixel position in A-scan image data constructed from the reflection intensity profile.

In the third process, the distance calculating circuitry 460 analyzes the second data acquired by the scanner 410 under the second scan control, to specify a position (second position) in the second data corresponding to the second site of the subject's eye E. For example, in the case where the second site is the retinal surface, the distance calculating circuitry 460 analyzes the second data acquired by applying the second OCT scan to the posterior eye segment region, to specify the second position corresponding to the retinal surface of the subject's eye E (typically the macular center). Typically, the second position is a signal position in the reflection intensity profile generated from the detection signal acquired in the second OCT scan, or a pixel position in A-scan image data constructed from the reflection intensity profile.

In the fourth process, the distance calculating circuitry 460 calculates the distance between the first site and the second site, based on the arm length difference calculated in the first process, the first position specified in the second process, and the second position specified in the third process.

Figure 5:
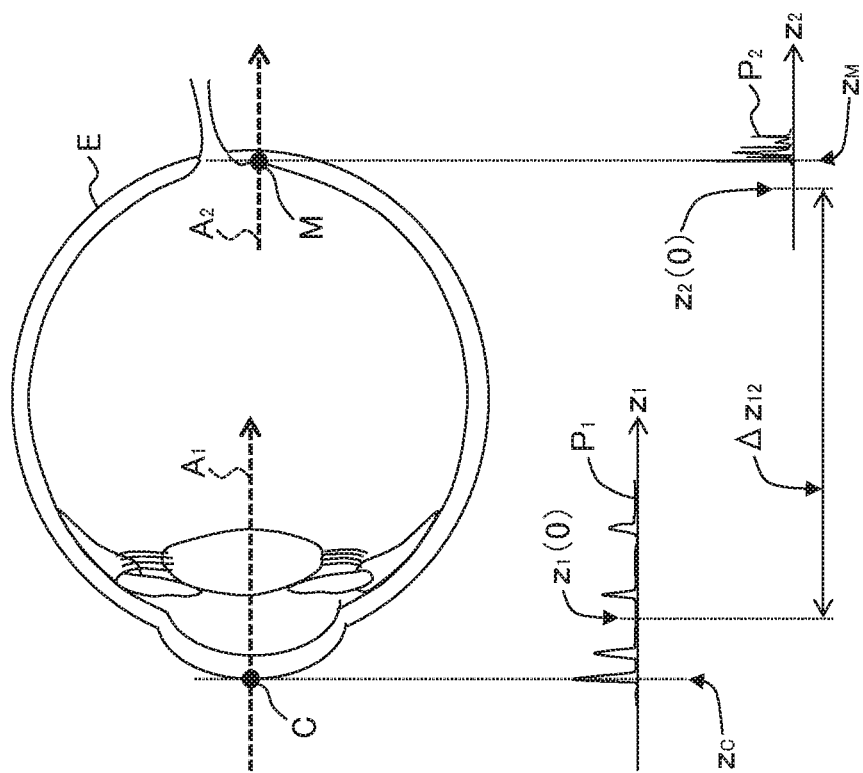
FIG. 5 is a schematic diagram illustrating an example of the operation that can be performed by the ophthalmic apparatus according to the exemplary embodiment.

Typically, in the fourth process, the distance calculating circuitry 460 determines a value of the axial length of the subject's eye E, based on the arm length difference calculated in the first process, the corneal apex position specified in the second process, and the macular center position specified in the third process. FIG. 5 illustrates a schema of the arithmetic processing.

The corneal apex of the subject's eye E is indicated by the reference symbol C, and the macular center is indicated by the reference symbol M. The reference symbols $A_1$ and $A_2$ indicate the first OCT scan and the second OCT scan, respectively. Each of the first OCT scan $A_1$ and the second OCT scan $A_2$ in the present example is an A-scan. FIG. 5 illustrates a case where the first OCT scan $A_1$ and the second OCT scan $A_2$ both are performed under appropriate alignment states. That is, FIG. 5 shows a case where the first OCT scan $A_1$ is performed on an A-line that passes through the corneal apex C, and the second OCT scan $A_2$ is performed on an A-line that passes through the macular center M.

The reflection intensity profile acquired by the first OCT scan $A_1$ is indicated by the reference symbol $P_1$, and the reflection intensity profile acquired by the second OCT scan $A_2$ is indicated by the reference symbol $P_2$. The z coordinate axis in which the first reflection intensity profile $P_1$ is defined is represented by "$z_1$", and the z coordinate axis in which the second reflection intensity profile $P_2$ is defined is represented by "$z_2$".

The first OCT scan $A_1$ on the anterior eye segment region is performed in a state that the coherence gate is disposed at an arbitrary position in the anterior eye segment. For example, the coherence gate is disposed at a position distant from the corneal apex C by a half distance of the corneal curvature radius in the +z direction. A bright spot is formed at this position. The reference symbol $z_1(0)$ indicates the coherence gate position applied at the time of the first OCT scan $A_1$ of the present example.

On the other hand, the second OCT scan $A_2$ for the posterior eye segment region is performed in a state that the coherence gate is disposed at an arbitrary position in the posterior eye segment. For example, the coherence gate is disposed in the vitreous body at a position near the retinal surface. The reference symbol $z_2(0)$ indicates the coherence gate position applied at the time of the second OCT scan $A_2$ of the present example.

The distance calculating circuitry 460 calculates the difference between the coherence gate position $z_1(0)$ applied at the time of the first OCT scan $A_1$ and the coherence gate position $z_2(0)$ applied at the time of the second OCT scan $A_2$. The difference is indicated by the reference symbol $\Delta z_{12}$ in FIG. 5, and corresponds to the arm length difference between the first OCT scan $A_1$ and the second OCT scan $A_2$. This process is an example of the first process described above.

The first reflection intensity profile $P_1$ includes a peak corresponding to the corneal front surface, a peak corresponding to the corneal back surface, a peak corresponding to the crystalline lens front surface, and a peak corresponding to the crystalline lens back surface. The distance calculating circuitry 460 specifies a peak corresponding to the corneal front surface from among the peaks in the first reflection intensity profile $P_1$. The peak specification includes, for example, a process of specifying the peak of maximum intensity. Alternatively, the peak specification may include a process of specifying the peak having the smallest $z_1$ coordinate value (i.e., the peak located on the most side) from among the peaks whose intensities exceed a predetermined threshold. The $z_1$ coordinate value of the peak corresponding to the corneal front surface thus specified is represented by "$z_C$". The $z_1$ coordinate value $z_C$ in the present example corresponds to the position of the corneal apex C. The process of determining the $z_1$ coordinate value $z_C$ is an example of the second process described above.

The second reflection intensity profile $P_2$ includes a peak corresponding to the retinal surface, and also a plurality of peaks corresponding to the retinal inner layers, and peaks corresponding to the choroid. The distance calculating circuitry 460 specifies a peak corresponding to the retinal surface from among the peaks in the second reflection intensity profile $P_2$. The peak specification includes, for example, a process of specifying the peak of maximum intensity. Alternatively, the peak specification may include a process of specifying the peak having the smallest $z_2$ coordinate value (i.e., the peak located on the most $-z_2$ side) from among the peaks having intensities exceeding a predetermined threshold. The $z_2$ coordinate value of the peak corresponding to the retinal surface thus specified is represented by "$z_M$". The $z_2$ coordinate value $z_M$ in the present example corresponds to the position of the macular center M. The process of determining the $z_2$ coordinate value $z_M$ is an example of the third process described above.

The distance calculating circuitry 460 calculates the distance (axial length) between the corneal apex C and the macular center M, based on the arm length difference $\Delta z_{12}$ calculated in the first process, the corneal apex position $z_C$ specified in the second process, and the pupil center position $z_M$ specified in the third process. In the example shown in FIG. 5, the axial length AL is calculated using the following formula: $AL=\Delta z_{12}+(z_1(0)-z_C)+(z_M-z_2(0))$. The positive signs and negative signs in the right hand side of the formula are determined according to the setting of the coherence gate position, the setting of the first site, the setting of the second site, etc. In general, the axial length AL is calculated using the following formula: $AL=\Delta z_{12}\pm|z_C-z_1(0)|\pm|z_M-z_2(0)|$. The process of calculating the distance, such as the axial length, is an example of the fourth process.

<Operations>

Figure 6:
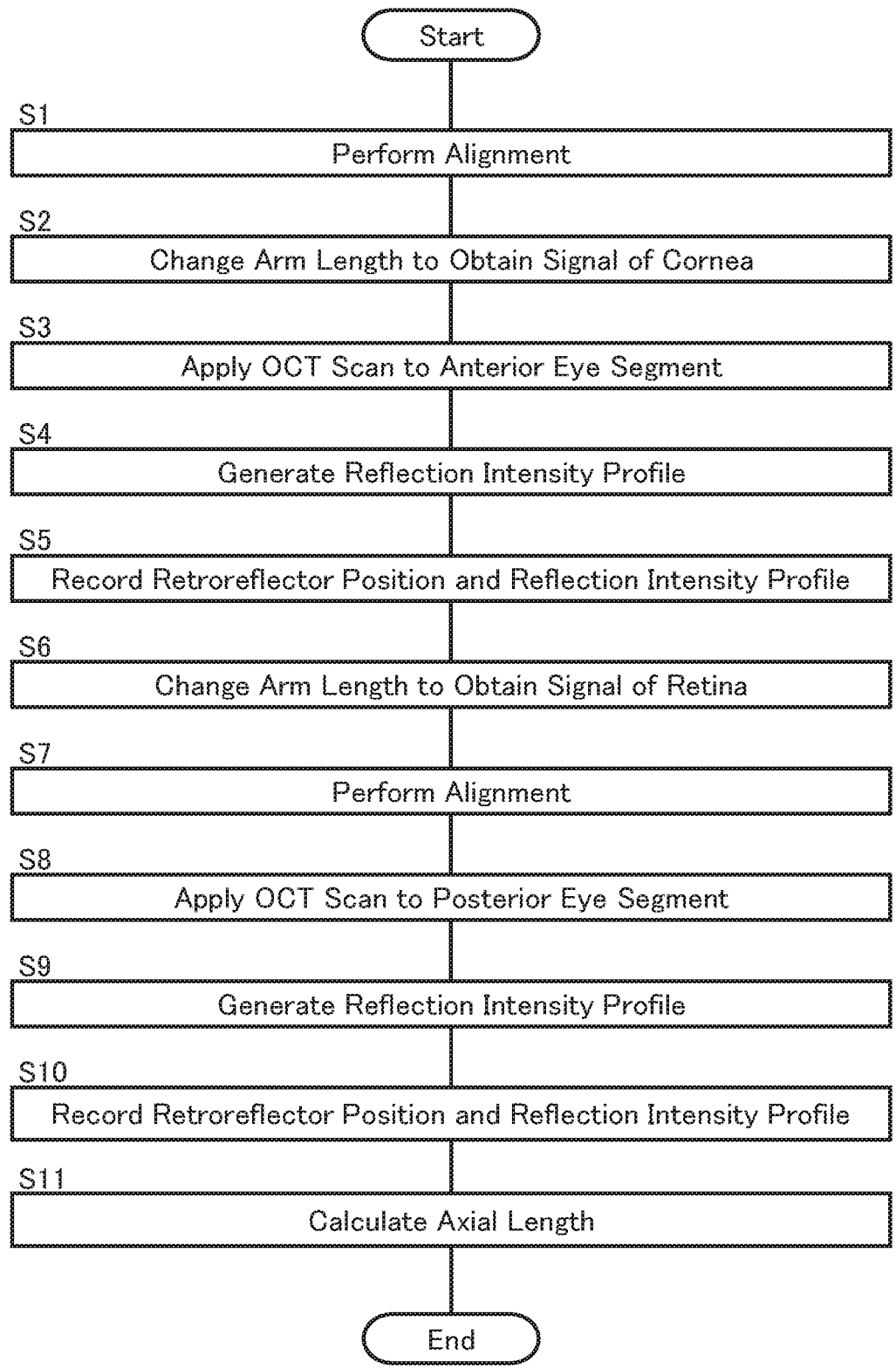
FIG. 6 is a flowchart illustrating an example of the operation that can be performed by the ophthalmic apparatus according to the exemplary embodiment.

Some examples of the operation of the ophthalmic apparatus 1 according to the present embodiment will be described. FIG. 6 shows an example of the operation of the ophthalmic apparatus 1. In the present operation example, a fixation target for macula imaging is presented to the subject's eye E.

(S1: Perform Alignment)

First, alignment of the ophthalmic apparatus 1 is performed with respect to the subject's eye E.

In the present example, the alignment controlling circuitry 440 first turns on the light emitting diode 51 of the alignment optical system 50. With this, a light beam is projected onto the anterior eye segment of the subject's eye E, and a bright spot is formed in the anterior eye segment. The two anterior eye segment cameras 300 photograph the anterior eye segment, onto which the light beam is being projected, from directions different from each other. As a result, a pair of anterior eye segment images in which the bright spot is photographed are obtained.

The deviation calculating circuitry 430 specifies the bright spot position from each of the pair of anterior eye segment images, and determines the deviation of the subject's eye E with respect to a predetermined reference position. The alignment controlling circuitry 440 controls the movement mechanism 150 so as to cancel the deviation calculated by the deviation calculating circuitry 430.

In the present example, the ophthalmic apparatus 1 repeatedly performs a series of processes at predetermined time intervals, the series of processes including anterior eye segment photography with the two anterior eye segment cameras 300, deviation calculation with the deviation calculation circuitry 430, and movement control with the alignment controlling circuitry 440. The series of processes allows gradual improvement of the alignment state and also maintenance of an appropriate alignment state. The maintenance of the appropriate alignment state is referred to as tracking.

(S2: Change Arm Length to Obtain Signal of Cornea)

After the appropriate alignment state has been achieved by step S1, the scan controlling circuitry 450 (and the data processing circuitry 230) changes any one or both of the measurement arm length and the reference arm length in such a way that a signal corresponding to the cornea of the subject's eye E can be obtained. Here, the measurement arm length is changed by controlling the retroreflector driver 41A, and the reference arm length is changed by controlling the retroreflector driver 114A.

Further, in consideration of the fact that the position of the cornea is determined by the working distance, the ophthalmic apparatus 1 may control a retroreflector driver (i.e., any one or both of the retroreflector driver 41A and the retroreflector driver 114A) by a predetermined control amount in such a way that a retroreflector (i.e., any one or both of the retroreflector 41 and the retroreflector 114) is disposed at a position corresponding to an arm length (i.e., any one or both of the measurement arm length and the reference arm length) at which a signal from the corneal position determined by the predetermined working distance can be detected.

The process in step S2 includes, for example, the process referred to as "Auto-Z" disclosed in Japanese Unexamined Patent Application Publication No. 2017-184874 filed by the present applicant. Auto-Z is an automatic process of searching for an appropriate arm length. The appropriate arm length here is an arm length with which the signal of the cornea can be obtained. Note that the arm length adjustment in step S2 may be performed by a process different from Auto-Z. further, a process called "Z-lock" disclosed in the same patent application publication may be performed in addition to Auto-Z. Z-lock is an automatic process of maintaining a preferred imaging state that has been achieved by Auto-Z.

The ophthalmic apparatus 1 may be configured to perform alignment in the same manner as in step S1 again, after the arm length adjustment in step S2.

Here, the OCT focusing lens 43 may be moved to set the focus position at a vicinity of the cornea. For example, since the position of the cornea is determined by the working distance as described above, the corresponding position of the OCT focusing lens 43 may be determined in advance and the OCT focusing lens 43 may be moved to that position.

Further, in consideration of that fact that the signal intensity from the front surface of the cornea is high, the OCT focusing lens 43 may be moved to focus on the retina at the time of acquiring the signal of the cornea. If this is the case, the OCT focusing lens 43 may be moved in an interlocking manner with the movement of the focusing optical system 60, or the OCT focusing lens 43 may be moved by a movement amount determined using the focusing optical system 60.

(S3: Apply OCT Scan to Anterior Eye Segment)

After the completion of the arm length adjustment in step S2, the scan controlling circuitry 450 performs control for applying an OCT scan to the anterior eye segment of the subject's eye E. In the present example, the scan controlling circuitry 450 performs the first scan control for causing the scanner 410 to perform an OCT scan on the anterior eye segment region including the corneal surface of the subject's eye E.

The OCT scan applied here is, for example, an A-scan. Some cases of applying other scan modes will be described later.

(S4: Generate Reflection Intensity Profile)

The scanner 410 (the image constructing circuitry 220 therein) generates a reflection intensity profile from the data acquired in the OCT scan of step S3. The reflection intensity profile generated here is data corresponding to the A-line to which the A-scan is applied in step S3.

(S5: Record Retroreflector Position and Reflection Intensity Profile)

The ophthalmic apparatus 1 (e.g., the distance calculating circuitry 460) records the position of the retroreflector at the time of the OCT scan of step S3 being performed, and the reflection intensity profile generated in step S4.

In the case where the measurement arm length has been changed in step S2, the position of the retroreflector 41 is recorded. In the case where the reference arm length has been changed in step S2, the position of the retroreflector 114 is recorded. Here, the position of the retroreflector 41 can be determined, for example, based on the content of the control for the retroreflector driver 41A, or determined by detection of the position of the retroreflector 41. Similarly, the position of the retroreflector 114 can be determined, for example, based on the content of the control for the retroreflector driver 114A or determined by detection of the position of the retroreflector 114.

(S6: Change Arm Length to Obtain Signal of Retina)

Next, the scan controlling circuitry 450 (and the data processing circuitry 230) changes any one or both of the measurement arm length and the reference arm length to obtain a signal corresponding to the retina of the subject's eye E. This process is performed in a similar manner to that in step S2.

(S7: Perform Alignment)

After the arm length adjustment in step S6 has been completed, the alignment of the ophthalmic apparatus 1 with respect to the subject's eye E is performed. The alignment is performed in the same manner as in step S1.

In the case where the OCT focusing lens 43 is moved to focus on the cornea or the vicinity thereof for acquiring the signal from the cornea (as described above), the OCT focusing lens 43 may be moved to focus on the retina at this stage. At this time, the OCT focusing lens 43 may be moved in an interlocking manner with the movement of the focusing optical system 60, or the OCT focusing lens 43 may be moved by a movement amount determined using the focusing optical system 60.

(S8: Apply OCT Scan to Posterior Eye Segment)

After the alignment in step S7 has been completed, the scan controlling circuitry 450 performs control for applying an OCT scan to the posterior eye segment of the subject's eye E. In the present example, the scan controlling circuitry 450 performs the second scan control for causing the scanner 410 to perform an OCT scan on the posterior eye segment region including the retinal surface of the subject's eye E.

The OCT scan applied here is, for example, an A-scan. Some cases of applying other scan modes will be described later.

(S9: Generate Reflection Intensity Profile)

The scanner 410 (the image constructing circuitry 220 therein) generates a reflection intensity profile from the data acquired in the OCT scan of step S8. The reflection intensity profile generated here is data corresponding to the A-line to which the A-scan is applied in step S8.

(S10: Record Retroreflector Position and Reflection Intensity Profile)

The ophthalmic apparatus 1 (e.g., the distance calculating circuitry 460) records the position of the retroreflector at the time of the OCT scan of step S8 being performed, and the reflection intensity profile generated in step S9. This process is performed in the same manner as in step S5.

(S11: Calculate Axial Length)

The distance calculating circuitry 460 calculates the distance between the corneal surface and the retinal surface based on the retroreflector position and the reflection intensity profile recorded in step S5 and the retroreflector position and the reflection intensity profile recorded in step S10.

In the present example, the distance calculating circuitry 460 first calculates the difference between the first arm length and the second arm length based on the retroreflector position recorded in step S5 (that is, the first arm length applied to the anterior eye segment OCT scan) and the retroreflector position recorded in step S10 (that is, the second arm length applied to the posterior eye segment OCT scan). Further, the distance calculating circuitry 460 analyzes the reflection intensity profile recorded in step S5 to specify a position corresponding to the corneal surface (the first position), and analyzes the reflection intensity profile recorded in step S10 to specify a position corresponding to the retinal surface (the second position). Then, the distance calculating circuitry 460 calculates the axial length of the subject's eye E based on the difference between the arm lengths, the first position, and the second position. This terminates the operation according to the present operation example (End).

Modifications of the First Embodiment

Some modifications applicable to the ophthalmic apparatus 1 according to the first embodiment will be described. Unless otherwise mentioned, the reference symbols used in the description of the ophthalmic apparatus 1 will be used in the following description.

First Modification Example

For example, if the subject's eye suffers from eye floaters (myodesopsia), turbidity/floaters moving in the vitreous body can adversely affect the posterior eye segment OCT scan.

In order to address this issue, a plurality of OCT scans may be applied to the posterior eye segment. Such repetitive OCT scan is performed by the scanner 410 under the control of the scan controlling circuitry 450. Each OCT scan therein is typically an A-scan, but is not limited thereto, and may be any scan mode such as a B-scan or a three dimensional scan.

An example of an applicable repetitive OCT scan (a plurality of OCT scans) is described. The ophthalmic apparatus of the present example first carries out an A-scan. In the case where the distance measurement cannot be appropriately performed even after the A-scan has been repeated a predetermined number of times (e.g., 10 times), the ophthalmic apparatus of the present example switches the scan mode from the A-scan mode to another scan mode. Another scan mode here is, for example, a B-scan. The judgment as to whether or not the distance measurement has been carried out appropriately includes, for example, comparing the intensity of the interference signal obtained by the OCT scan (A-scan at this stage) with a predetermined threshold. If the interference signal intensity is equal to or higher than the threshold value, the ophthalmic apparatus of the present example determines that the distance measurement has been appropriately performed. On the other hand, if the interference signal intensity is less than the threshold value, the ophthalmic apparatus of the present example determines that the distance measurement has not been appropriately performed. The scan line length of the B-scan of the present example is optional, and is typically shorter than that of normal B-scans (e.g., 1 mm in length for the present example). In the case where the distance measurement cannot be appropriately performed even after the B-scan has been repeated the predetermined number of times (e.g., 10 times), the ophthalmic apparatus of the present example again switches the scan mode from the B-scan to another scan mode. The scan pattern of this another scan mode is, for example, a radial scan. The determination as to whether or not the distance measurement with the B-scan has been carried out appropriately is performed in the same manner as in the case of the A-scan. The size of the radial scan in the present example is arbitrary, and typically smaller than that of normal radial scans (e.g., each scan line having a length of 1 mm for the present example). By performing the scan mode switching as described above, a signal corresponding to the retina can be obtained at some stage.

More generally, the ophthalmic apparatus of the present example first applies the first scan mode. The ophthalmic apparatus of the present example determines whether or not the data obtained by the OCT scan in the first scan mode meets a predetermined condition. In the case where the condition is not satisfied even after the OCT scan in the first scan mode has been repeated a predetermined number of times, the ophthalmic apparatus of the present example switches the scan mode from the first scan mode to the second scan mode. The ophthalmic apparatus of the present example determines whether the data obtained by the OCT scan in the second scan mode satisfies a predetermined condition. In the event where the condition is not satisfied even after the OCT scan in the second scan mode has been repeated a predetermined number of times, the ophthalmic apparatus of the present example switches the scan mode from the second scan mode to the third scan mode. In this way, the ophthalmic apparatus of the present example determines whether or not appropriate data has been obtained by the OCT scan in the q-th scan mode by considering a predetermined condition. In the event where appropriate data cannot be obtained, the ophthalmic apparatus switches the scan mode from the q-th scan mode to the (q+1)-th scan mode to perform an OCT scan (where q is an integer 1 or larger). Here, at least two scan modes are set in advance, and one or more scan mode transition conditions are also set in advance. Further, for example, the (q+1)-th scan mode is applied to a position different from the position to which the q-th scan mode is applied, and/or, the (q+1)-th scan mode is applied to a wider area than the area to which the q-th scan mode is applied. By performing such a scan mode transition one after another, it becomes possible to detect a signal corresponding to the retina at some stage, even in the cases where floaters are present in the subject's eye.

The orientation of the optical scanner 44 (mirrors therein) may or may not be constant in the plurality of OCT scans. In the case of constant orientation, even when one OCT scan receives the influence of turbidity or floaters by the movement of the turbidity or floaters in the vitreous body, some other OCT scans may not be affected thereby. In the case of inconstant orientation, the influence of the turbidity or floaters in the vitreous body can be positively avoided. However, in the latter case, it may be desirable to restrict the area of change in the orientation of the optical scanner 44 in such a way that the target site for the distance measurement (e.g., the macular center) does not deviate from the area to which OCT scans are applied. In particular, in the case of applying A-scans, it is required to restrict the range of the change in the orientation of the optical scanner 44 to a very small area. The area of the change in the orientation of the optical scanner 44 may be set in advance, for example, according to the scan mode to be applied.

The scanner 410 generates a reflection intensity profile or image data from a detection signal obtained by each of the plurality of OCT scans. Thereby, a data group (a plurality of pieces of data) corresponding to the plurality of OCT scans can be obtained.

The distance calculating circuitry 460 can acquire a single piece of data from the data group acquired through the plurality of OCT scans, and perform the distance calculation using the single piece of data acquired.

For example, the distance calculating circuitry 460 can generate the single piece of data by synthesizing (that is, averaging) at least two pieces of data from among the plurality of pieces of data included in the data group. By averaging two or more pieces of data obtained through two or more OCT scans applied to (substantially) the same site of the subject's eye E, noise due to turbidity or floaters in the vitreous body etc. can be reduced or eliminated.

In another example, the distance calculating circuitry 460 may be configured to select one piece of data from the data group acquired through the plurality of OCT scans. In the data selection, for example, a predetermined evaluation value (e.g., contrast) that can be obtained from the data may be referred to. Thereby, even in the event where any of the plurality of pieces of data included in the data group is affected by the turbidity or floaters in the vitreous body, non-affected or less-affected data can be selected.

In addition, in the case where the single piece of data obtained by the distance calculating circuitry 460 does not meet a predetermined condition (e.g., contrast condition), the ophthalmic apparatus of the present example may perform the posterior eye segment OCT scan again and/or display a message that prompts the user to instruct re-execution of the posterior eye segment OCT scan.

Second Modification Example

In order to accurately measure the distance between two sites of the subject's eye E, it is necessary to accurately specify the two sites. To that end, an OCT scan may be applied to a three dimensional region of the subject's eye E. Examples of scan modes for that purpose include a three dimensional scan, a radial scan, and a multi-line cross scan.

The radial scan is a scan mode composed of a plurality of line scans (a plurality of B-scans) arranged in a radial pattern, and the multi-line cross scan is a scan mode composed of two groups of line scans orthogonal to each other.

In some examples, the scan controlling circuitry 450 causes the scanner 410 to perform an OCT scan on a three dimensional region of the subject's eye E in at least one of the anterior eye segment OCT scan and the posterior eye segment OCT scan.

Typically, the scan controlling circuitry 450 may cause the scanner 410 to perform an OCT scan on a three dimensional region including the corneal surface of the subject's eye E in the anterior eye segment OCT scan. In a state where an appropriate alignment is being maintained, an OCT scan is applied to a three dimensional region of the anterior eye segment including the corneal apex of the subject's eye E.

In addition, the scan controlling circuitry 450 causes the scanner 410 to perform an OCT scan on a three dimensional region including the retinal surface of the subject's eye E in the posterior eye segment OCT scan. In a state where an appropriate alignment is being maintained, an OCT scan is applied to a three dimensional region of the posterior eye segment including the macular center of the subject's eye E.

The distance calculating circuitry 460 may analyze the data acquired by the OCT scan from the three dimensional region of the subject's eye E, to specify a feature position corresponding to a feature point of the subject's eye E.

Typically, the distance calculating circuitry 460 may analyze the data acquired by the OCT scan from the three dimensional region of the anterior eye segment including the corneal apex of the subject's eye E, to specify a feature position corresponding to the corneal apex. This process includes, for example, a process of specifying an image region corresponding to the corneal surface from the data of the three dimensional region of the anterior eye segment, and a process of specifying a feature position (corneal apex position) corresponding to the corneal apex based on the shape of the image region.

Further, the distance calculating circuitry 460 may analyze the data acquired by the OCT scan from the three dimensional region of the posterior eye segment including the macular center of the subject's eye E, to specify a feature position corresponding to the macular center. This process includes, for example, a process of specifying an image region corresponding to the retinal surface (the inner limiting membrane or the like) from the data of the three dimensional region of the posterior eye segment, and a process of specifying a feature position (macular center position) corresponding to the macular center based on the shape of the image region, the position of a predetermined tissue, the position of a predetermined site, etc. An example of the predetermined tissue is any sub-tissue (layer tissue) of the retina, and an example of the predetermined site is the optic nerve head.

The distance calculating circuitry 460 calculates the length of a line segment whose one end is placed at the feature position specified. The length of the line segment is the distance for measurement purposes.

In the case where the corneal apex position is specified from the data acquired by the anterior eye segment OCT scan, and also the macular center position is specified from the data acquired by the posterior eye segment OCT scan, the distance calculating circuitry 460 calculates the distance of the line segment connecting the corneal apex position and the macular center position. The distance calculated in this way corresponds to the axial length of the subject's eye E.

Effects

The effects of the ophthalmic apparatus 1 according to the first embodiment and the modification examples thereof will be described.

The ophthalmic apparatus 1 includes the scanner 410, the movement mechanism 150, the deviation detector 420, the scan controlling circuitry 450, the alignment controlling circuitry 440, and the distance calculating circuitry 460.

The scanner 410 is configured to apply an OCT scan to the subject's eye E. The movement mechanism 150 is configured to move at least part of the scanner 410. The deviation detector 420 is configured to measure the deviation of the subject's eye E with respect to a predetermined reference position.

The scan controlling circuitry 450 is configured to perform the first scan control and the second scan control. The first scan control causes the scanner 410 to perform an OCT scan on the first region (e.g., the anterior eye segment region) including the first site of the subject's eye E (e.g., the corneal surface). The second scan control causes the scanner 410 to perform an OCT scan on the second region (e.g., the posterior eye segment region) including the second site different from the first site (e.g., the retinal surface). The OCT scan performed under the first scan control is referred to as the first OCT scan, and the OCT scan performed under the second scan control is referred to as the second OCT scan.

The alignment controlling circuitry 440 is configured to perform the first alignment control and the second alignment control. In the first alignment control, the alignment controlling circuitry 440 controls the movement mechanism 150 based on the first deviation information of the subject's eye E acquired by the deviation detector 420 prior to the first scan control. In the second alignment control, the alignment controlling circuitry 440 controls the movement mechanism 150 based on the second deviation information of the subject's eye E acquired by the deviation detector 420 prior to the second scan control. Note that the ophthalmic apparatus 1 may perform alignment in the x direction and the y direction as well as alignment in the z direction.

The distance calculating circuitry 460 is configured to calculate the distance between the first site and the second site (e.g., the axial length) based on the first data acquired by the scanner 410 under the first scan control and the second data acquired by the scanner 410 under the second scan control.

According to the ophthalmic apparatus 1 configured in this way, the alignment is performed prior to both the first OCT scan and the second OCT scan. Therefore, both the first OCT scan and the second OCT scan may be performed in appropriate alignment conditions. Thus, for example, in the case of performing the second OCT scan after the first OCT scan, even if the subject's eye moves during the period from the first OCT scan to the second OCT scan, the alignment controlling circuitry 440 controls may perform the alignment on the moved subject's eye prior to the second OCT scan. This ensures the reliability of the distance measurement.

As an optional configuration, the scanner 410 of the ophthalmic apparatus 1 includes the interference optical system that includes the measurement arm that guides the measurement light to the subject's eye, and the reference arm that guides the reference light. Further, as an optional configuration, the scanner 410 includes the arm length changer that is provided in at least one of the measurement arm and the reference arm, and changes the arm length under the control of the scan controlling circuitry 450. The combination of the retroreflector 41 and the retroreflector driver 41A is an example of the arm length changer provided in the measurement arm. The combination of the retroreflector 114 and the retroreflector driver 114A is an example of the arm length changer provided in the reference arm.

In addition, as an optional configuration, the distance calculating circuitry 460 may perform the following series of processes: (1) the process of calculating the difference (the arm length difference) between the first arm length applied at the time of the first scan control (the first OCT scan) and the second arm length applied at the time of the second scan control (the second OCT scan); (2) the process of analyzing the first data acquired through the first OCT scan to specify the first position corresponding to the first site of the subject's eye E (e.g., a signal position corresponding to the corneal surface); (3) the process of analyzing the second data acquired in the second OCT scan to specify the second position corresponding to the second site of the subject's eye E (e.g., a signal position corresponding to the retinal surface); and (4) the processing of calculating the distance between the first site and the second site (e.g., axial length) based on the arm length difference calculated by the process in (1), the first position specified by the process in (2), and the second position specified by the process in (3).

Such an optional configuration is capable of providing specific and concrete processing for calculating the distance between the first site and the second site of the subject's eye E.

As an optional configuration, the scan controlling circuitry 450 may cause the scanner 410 to perform a plurality of times of OCT scans in at least one of the first scan control (the first OCT scan) and the second scan control (the second OCT scan). If this is the case, the distance calculating circuitry 460 may acquire a single piece of data from the data group acquired by the plurality of times of OCT scans. Here, the distance calculating circuitry 460 can generate the single piece of data by performing averaging on the data group acquired by the plurality of OCT scans. Further, the distance calculating circuitry 460 may calculate the distance between the first site and the second site using the single piece of data acquired.

According to the optional configuration described above, even in the case where the turbidity or floaters moving in the vitreous body adversely affects the posterior eye segment OCT scan, the noise caused by the turbidity or floaters may be reduced or eliminated, and/or, the data that is not affected by the turbidity or floaters or data that is less affected may be selected. This makes it possible to improve the reliability of the distance measurement.

As an optional configuration, the scan controlling circuitry 450 may cause the scanner 410 to perform an OCT scan on a three dimensional region of the subject's eye E in at least one of the first scan control (the first OCT scan) and the second scan control (the second OCT scan). If this is the case, the distance calculating circuitry 460 may analyzes the data acquired by the OCT scan on the three dimensional region to specify the feature position corresponding to a feature point of the subject's eye E. Further, the distance calculating circuitry 460 may calculate a length of a line segment whose one end is placed at the feature position, as the distance between the first site and the second site.

As the first typical example, the scan controlling circuitry 450 may cause the scanner 410 to perform an OCT scan on a three dimensional region including the corneal surface of the subject's eye E in the first scan control (the first OCT scan). Further, the distance calculating circuitry 460 may analyzes the data acquired by the OCT scan on the three dimensional region to specify the feature position corresponding to the corneal apex of the subject's eye E. If this is the case, the distance calculating circuitry 460 may calculate the length of a line segment whose one end is placed at the corneal apex, as the distance between the first site and the second site.

As the second typical example, the scan controlling circuitry 450 may cause the scanner 410 to perform an OCT scan on a three dimensional region including the retinal surface of the subject's eye E in the second scan control (the second OCT scan). Further, the distance calculating circuitry 460 may analyzes the data acquired by the OCT scan on the three dimensional region to specify the feature position corresponding to the macular center of the subject's eye E. If this is the case, the distance calculating circuitry 460 can calculate the length of a line segment whose one end is placed at the macular center, as the distance between the first site and the second site.

By combining the first and second typical examples, the length of the line segment whose one end is placed at the corneal apex and the other end is placed at the macular center, which corresponds to the axial length of the subject's eye E, can be determined.

As an optional configuration, the deviation detector 420 includes the alignment optical system 50 (corresponding to the projection system), the two (or more) anterior eye segment cameras 300 (corresponding to the two or more cameras), and the deviation calculating circuitry 430. The alignment optical system 50 is configured to project a light beam onto the anterior eye segment of the subject's eye E. The two (or more) anterior eye segment cameras 300 are configured to photograph the anterior eye segment of the subject's eye E from directions different from each other. The deviation calculating circuitry 430 is configured to calculate the deviation of the subject's eye E with respect to a predetermined reference position based on positions of images of the light beam (bright spot images) in the two (or more) anterior eye segment images acquired by the two or more anterior eye segment cameras 300.

This optional configuration may provide a specific and concrete configuration and processing for measuring the deviation of the subject's eye E with respect to the predetermined reference position.

In addition, any of the items described in the first embodiment (configurations, elements, processing, processes, operations, actions, functions, etc.) and/or any of known items may be combined with the ophthalmic apparatus described here.

The first embodiment provides a method of controlling an ophthalmic apparatus. The ophthalmic apparatus includes a scanner (410) configured to apply an OCT scan to a subject's eye, a movement mechanism (150) configured to move at least part of the scanner (410), and a deviation detector (420) configured to measure deviation of the subject's eye (E) with respect to a predetermined reference position.

The controlling method includes the first alignment control step, the first scan control step, the second alignment control step, the second scan control step, and a distance calculation step.

The first alignment control step controls the movement mechanism (150) based on the first deviation information of the subject's eye (E) acquired by the deviation detector (420). The first scan control step causes the scanner (410) to perform an OCT scan on the first region including the first site of the subject's eye (E). The OCT scan performed under the first scan control step is referred to as the first OCT scan.

The second alignment control step controls the movement mechanism (150) based on the second deviation information of the subject's eye (E) acquired by the deviation detector (420). The second scan control step causes the scanner (410) to perform an OCT scan on the second region including the second site different from the first site of the subject's eye (E). The OCT scan performed under the second scan control step is referred to as the second OCT scan.

The distance calculation step calculates a distance between the first site and the second site, based on the first data acquired by the scanner (410) in the first scan control step and the second data acquired by the scanner (410) in the second scan control step.

According to the method of controlling the ophthalmic apparatus carried out in this way, the alignment is performed prior to both the first OCT scan and the second OCT scan. Therefore, both the first OCT scan and the second OCT scan may be performed in appropriate alignment conditions. Thus, the reliability of the distance measurement can be ensured by the controlling method provided by the first embodiment.

In addition, any or the items (configurations, elements, processing, processes, operations, actions, functions, etc.) described in the first embodiment and/or any of known items may be combined with the controlling method.

It is possible to configure a program for causing a computer to execute such the above-described controlling method. The program may include, for example, any of the aforementioned programs for operating the ophthalmic apparatus 1 of the first embodiment or any of its modification examples.

Further, a computer-readable non-transitory recording medium storing such a program may be created. The non-transitory recording medium may be of any form or aspect, and examples thereof include magnetic disks, optical disks, magneto-optical disks, semiconductor memories, and the like.

Second Embodiment

As described above, the first embodiment is designed to improve the reliability of the distance measurement of the subject's eye by performing alignment prior to both the first and second OCT scans. In other words, the first embodiment is designed to improve the reliability of the distance measurement through improving the reliability of the first and second OCT scans.

On the other hand, the second embodiment is designed to improve the reliability of the distance measurement by means of data processing for correcting an alignment error involved in OCT scans.

Hereinafter, the description of the items same as those of the first embodiment will be omitted unless otherwise mentioned. Further, among the elements included in the second embodiment, the same elements as those in the first embodiment are given the same reference symbols as the corresponding elements in the first embodiment. Further, in the following description, some elements of the first embodiment will be referred to as required.

<Configurations>

Figure 7:
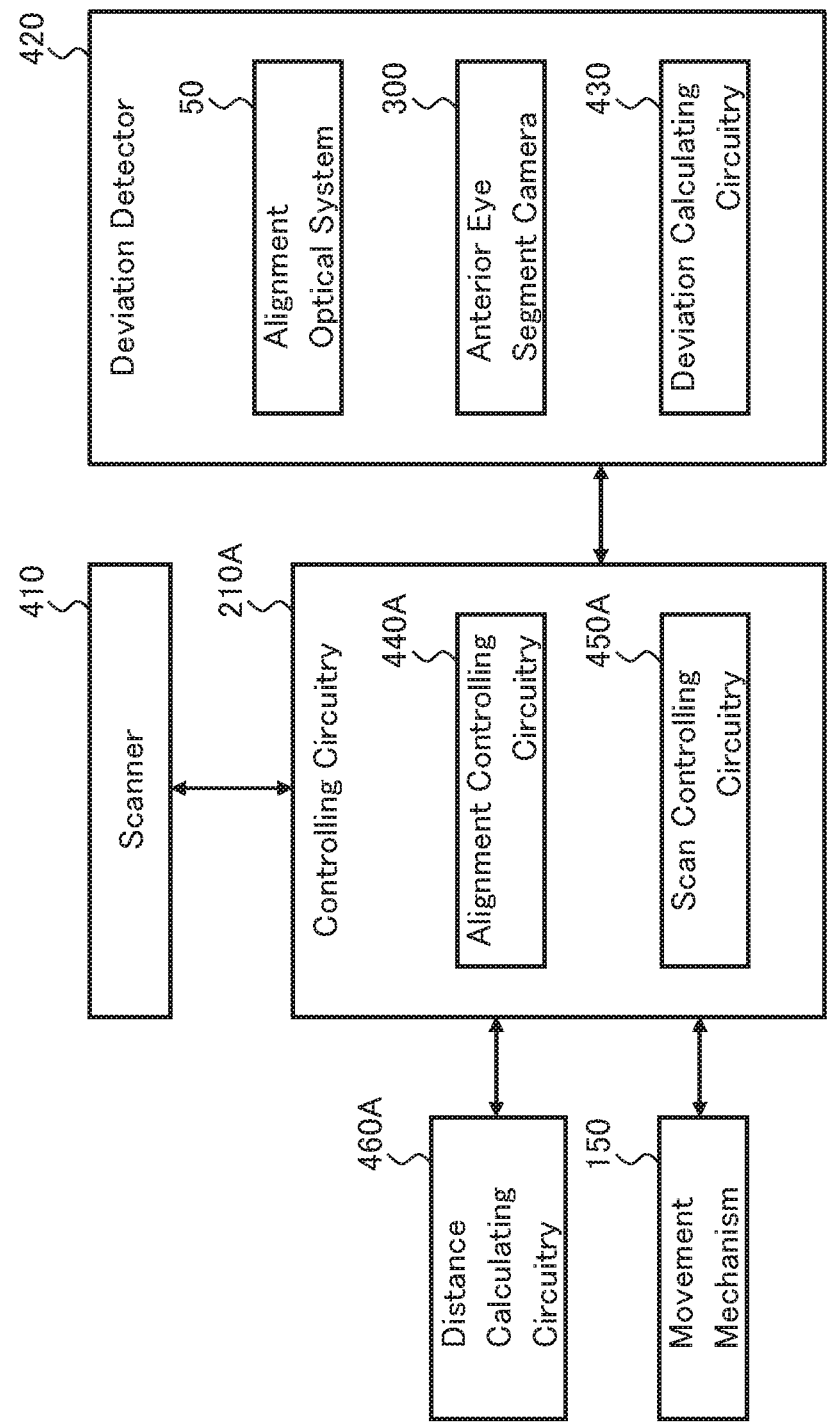
FIG. 7 is a schematic diagram illustrating an example of the configuration of an ophthalmic apparatus according to an exemplary embodiment.

FIG. 7 shows an example of the configuration of an ophthalmic apparatus according to the present embodiment. The ophthalmic apparatus 1A has the same hardware configuration as that of the ophthalmic apparatus 1 according to the first embodiment (see FIG. 1, FIG. 2, FIG. 3A, FIG. 4A, and FIG. 4B). The configuration shown in FIG. 7 is applied in place of the configuration shown in FIG. 3B of the first embodiment.

In the ophthalmic apparatus 1A, the scanner 410, the deviation detector 420, and the movement mechanism 150 respectively have the same configurations, functions, and actions as those of the first embodiment.

The scanner 410 applies an OCT scan to the subject's eye E to acquire data. As in the first embodiment, the scanner 410 includes an interference optical system that includes a measurement arm that guides the measurement light LS to the subject's eye E and a reference arm that guides the reference light LS. Further, as in the first embodiment, the scanner 410 includes an arm length changer provided in any one or both of the measurement arm and the reference arm.

The deviation detector 420 measures the deviation of the subject's eye E with respect to a predetermined reference position. As in the first embodiment, the deviation detector 420 may include the alignment optical system 50, the anterior eye segment cameras 300, and the deviation calculating circuitry 430. The deviation detector 420 shown in FIG. 7 is an example applicable to the case where the position of the subject's eye E is defined as the bright spot position. When another definition (for example, the pupil center position or the corneal apex position) is employed, a configuration according thereto is applied.

The alignment controlling circuitry 440A, which will be described later, is configured to perform alignment control based on the measurement result of the deviation (deviation information) acquired by the deviation detector 420. Further, the distance calculating circuitry 460A described later is configured to calculate a distance in the subject's eye E in consideration of the deviation information acquired by the deviation detector 420.

The ophthalmic apparatus 1A performs the first OCT scan on the first region (e.g., the anterior eye segment region) including the first site of the subject's eye E (e.g., the corneal surface), and the second OCT scan on the second region (e.g., the posterior eye segment region) including the second site (e.g., the retinal surface). Details of the first OCT scan and second OCT scan will be described later. Note that the order of execution of the first OCT scan and the second OCT scan is optional.

The deviation detector 420 is configured to perform the first deviation measurement corresponding to the first OCT scan to acquire the first deviation information, and perform the second deviation measurement corresponding to the second OCT scan to acquire the second deviation information.

The first deviation measurement is performed at any timing such as before, during, or after the execution of the first OCT scan. Similarly, the second deviation measurement is performed at any timing such as before, during, or after the execution of the second OCT scan. Typically, the first deviation measurement is performed immediately before, during, or immediately after the first OCT scan, and the second deviation measurement is performed immediately before, during, or immediately after the second OCT scan.

The distance calculating circuitry 460A, which will be described later, is configured to calculate a predetermined distance (distance between predetermined sites) in the subject's eye E in consideration of any one or both of the first deviation information and the second deviation information acquired by the deviation detector 420. Further, the alignment controlling circuitry 440A described later is configured to perform alignment control based on any one of the first deviation information and the second deviation information acquired by the deviation detector 420. Note that the configuration in which the alignment control (the first alignment control) is performed based on the first deviation information and the alignment control (the second alignment control) is performed based on the second deviation information, corresponds to the first embodiment.

As in the first embodiment, the movement mechanism 150 is configured to move the scanner 410 (in particular, the measurement arm of the interference optical system) relative to the subject's eye E.

The alignment controlling circuitry 440A and the scan controlling circuitry 450A are provided in the controlling circuitry 210A. The controlling circuitry 210A is provided in place of the controlling circuitry 210 of the first embodiment. The controlling circuitry 210A includes a processor, and controls each part of the ophthalmic apparatus 1A. The controlling circuitry 210A includes main controlling circuitry and a memory (both not shown). The controlling circuitry 210A is realized by the cooperation of hardware including a circuit (circuitry) and controlling software.

As in the first embodiment, the alignment controlling circuitry 440A performs the alignment control for controlling the movement mechanism 150 based on the deviation information acquired by the deviation detector 420.

The scan controlling circuitry 450A is configured to perform the first scan control and the second scan control. The first scan control causes the scanner 410 to perform an OCT scan on the first region (e.g., the anterior eye segment region) including the first site of the subject's eye E (e.g., the corneal surface). The second scan control causes the scanner 410 to perform an OCT scan on the second region (e.g., the posterior eye segment region) including the second site different from the first site (e.g., the retinal surface). The first scan control and the second scan control are performed in the same manner as those executed by the scan controlling circuitry 450 of the first embodiment. The OCT scan performed under the first scan control is referred to as the first OCT scan, and the OCT scan performed under the second scan control is referred to as the second OCT scan.

As described above, the deviation detector 420 performs the deviation measurement of the subject's eye E before, during, or after the execution of the first scan control to acquire the first deviation information, and performs the deviation measurement of the subject's eye E before, during, or after the execution of the second scan control to acquire the second deviation information.

The distance calculating circuitry 460A is configured to calculate a distance (e.g., the axial length) between the first site (e.g., the corneal surface) and the second site (e.g., the retinal surface) of the subject's eye E, based on any one or both of the first deviation information and the second deviation information, the first data acquired in the first OCT scan, and the second data acquired in the second OCT scan.

In other words, the distance calculating circuitry 460A executes the distance calculation in consideration of any one or both of the alignment error at the time of performing the first OCT scan (the first deviation information) and the alignment error at the time of performing the second OCT scan (the second deviation information).

The distance calculating circuitry 460A performs, for example, the following series of processing. In the first process, the distance calculating circuitry 460A calculates the difference (the arm length difference) between the first arm length applied at the time of the first OCT scan and the second arm length applied at the time of the second OCT scan. In the second process, the distance calculating circuitry 460A analyzes the first data acquired by the first OCT scan to specify the first position corresponding to the first site of the subject's eye E (e.g., the signal position corresponding to the corneal surface). In the third process, the distance calculating circuitry 460A analyzes the second data acquired by the second OCT scan to specify the second position corresponding to the second site of the subject's eye E (e.g., the signal position corresponding to the retinal surface). The first to third processes are respectively performed in the same manner as those processes in the first embodiment. In the fourth process, the distance calculating circuitry 460A calculates the distance between the first site and the second site, based on the arm length difference calculated in the first process, the first position specified in the second process, the second position specified in the third process, and the deviation information (i.e., at least one of the first deviation information and the second deviation information) acquired by the deviation detector 420.

An example of such arithmetic processing will be described with referring to FIG. 8. As in FIG. 5 of the first embodiment, the reference symbol C indicates the corneal apex of the subject's eye E, and the reference symbol M indicates the macular center. Further, the straight line Ax passing through the corneal apex C and the macular center M indicates the eye axis of the subject's eye E.

The reference symbol K indicates the curvature center of the corneal surface at the corneal apex C. The curvature center K is the center of the curvature circle (i.e., the osculating circle) at the corneal apex C. The radius of the curvature circle, that is, the curvature radius of the corneal surface at the corneal apex C is denoted by r.

The reference symbol G indicates the path (incident path) of the measurement light LS projected onto the macular center M. The reference symbol H indicates the intersection point of the incident path G and the corneal surface of the subject's eye E, that is, the incident position of the measurement light LS on the subject's eye E.

The deviation (i.e., the height) of the incident path G with respect to the eye axis Ax is denoted by h. Assuming that the shape of the cornea surface is substantially spherical, or assuming that the height h is sufficiently small (that is, assuming that the alignment error is sufficiently small), it can be considered that the distance between the incident position H and the curvature center K is equal to the curvature radius r at the corneal apex C.

The angle formed by the eye axis Ax and the line segment connecting the incident position H and the curvature center K, is denoted by θ. Further, the angle formed by the eye axis Ax and the line segment connecting the incident position H and the macular center M, is denoted by φ.

The length of the line connecting the incident position H and the macular center M, is denoted by ALm. The length ALm corresponds to the measurement value of the axial length of the subject's eye E obtained from the data acquired by the OCT scan using the measurement light LS projected onto the macular center M along the incident path G.

The axial length of the subject's eye E (the true value) is denoted by AL. In addition, the distance between the corneal apex C and the incident position H in the direction along the eye axis Ax, that is, the magnitude of the eye-axis-direction (Ax-direction) component of the vector whose initial point is located at the corneal apex C and terminal point is located at the incident position H, is denoted by AL1. Further, the distance between the incident position H and the macular center M in the direction along the eye axis Ax, that is, the magnitude of the eye-axis-direction (Ax-direction) component of the vector whose initial point is located at the macular center M and terminal point is located at the incident position H is denoted by AL2.

Figure 8:
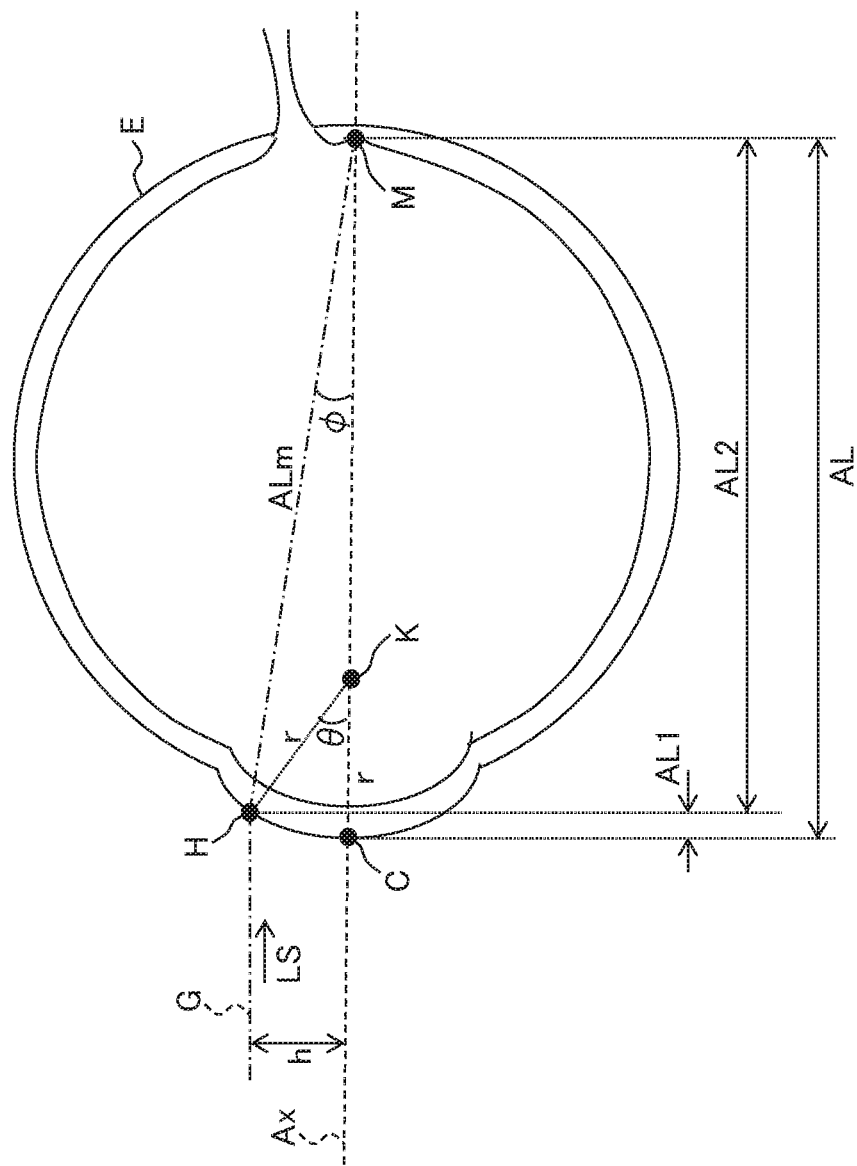
FIG. 8 is a schematic diagram illustrating an example of the operation that can be performed by the ophthalmic apparatus according to the exemplary embodiment.

As apparent from FIG. 8, the axial length AL is represented by the following formula: $AL=AL1+AL2=(r-r^*\cos\theta)+ALm\times\cos\varphi=(r-r^*\cos(\arcsin(h/r)))+ALm^*\cos(\arcsin(h/ALm))$.

Here, the corneal curvature radius r is assumed to be obtained in advance by a corneal shape measuring apparatus such as a keratometer. Further, the height h is an alignment error in the xy direction measured by the deviation detector 420 and is included in the deviation information. Further, the axial length measurement value ALm is a value of the axial length obtained by the ophthalmic apparatus 1A in the same manner as in the first embodiment. By substituting the values r, h, and ALm into the above formula, the axial length AL can be calculated.

The distance calculating circuitry 460A stores the above formula and the corneal curvature radius value (r) of the subject's eye E in advance, for example. The distance calculating circuitry 460A calculates the axial length (AL) of the subject's eye E, by substituting the following values into the above formula: the corneal curvature radius value (r); the deviation (h) in the xy direction included in the deviation information acquired by the deviation detector 420; and the value (ALm) of the axial length measured using the OCT scan.

Note that the present example describes the case where an alignment error in the xy direction is present at the time of performing the posterior eye segment OCT scan. It is clear to those skilled in the art that similar calculations may be applied to the case where an alignment error in the xy direction is present at the time of performing the anterior eye segment OCT scan, and the case where alignment errors are present at the time of performing both the anterior eye segment OCT scan and the posterior eye segment OCT scan.

Further, the present example considers only the refraction of the measurement light LS on the corneal surface; however, other refractive index boundaries may also be considered. For example, the refraction of the measurement light LS on refractive index boundaries such as the back surface of the cornea, the surface of the crystalline lens, and/or the back surface of the crystalline lens, may be considered.

In addition to the alignment error in the xy direction, the alignment error in the z direction may also be considered. The alignment error in the z direction is obtained by the deviation detector 420 as in the first embodiment.

<Operations>

Some examples of the operation of the ophthalmic apparatus 1A according to the present embodiment will be described. Described below are the first operation example and the second operation example. The first operation example performs the distance calculation in consideration of both the first deviation information and the second deviation information. The second operation example performs the distance calculation in consideration of the second deviation information while using the first deviation information for alignment.

First Operation Example

Figure 9:
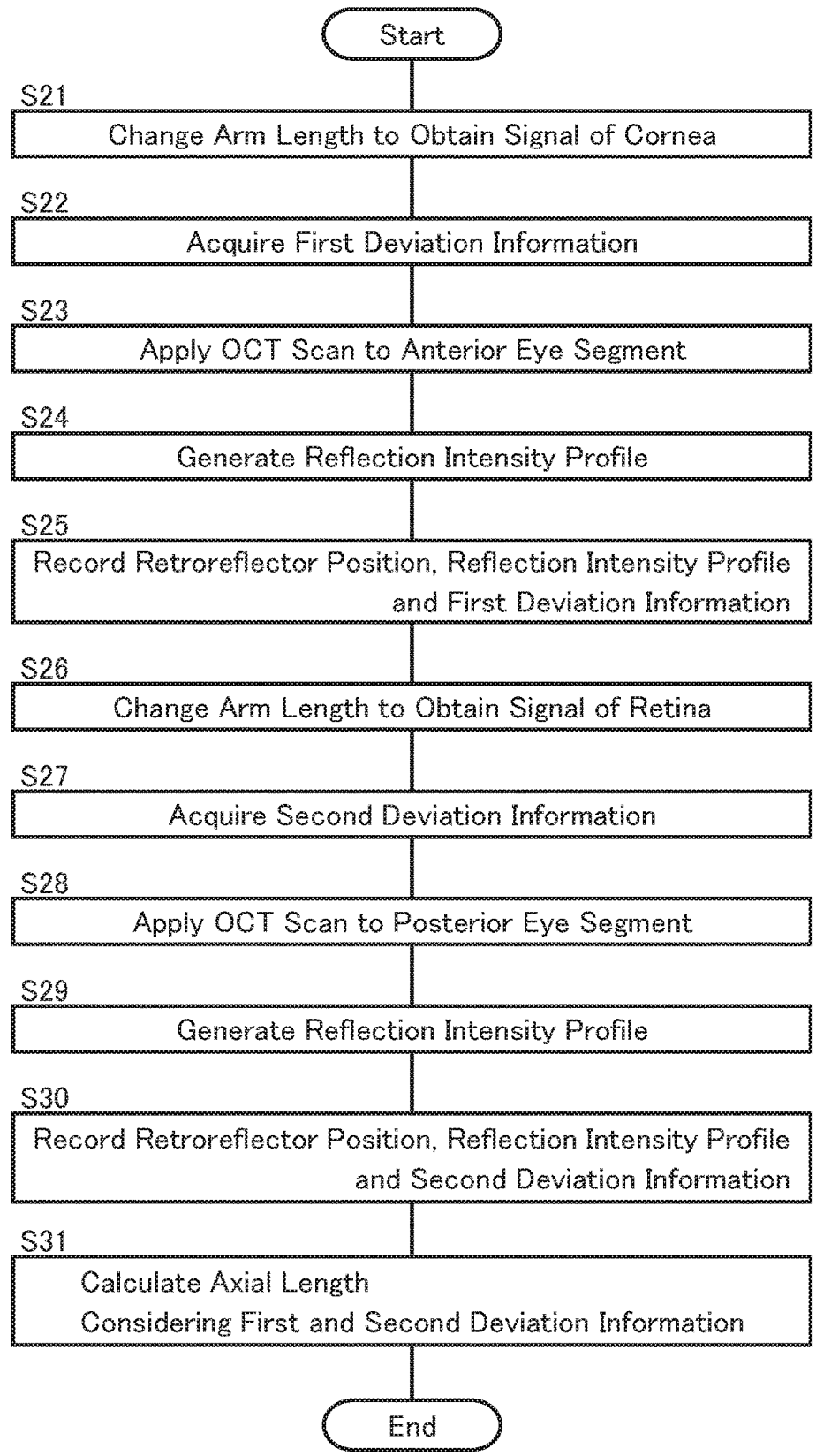
FIG. 9 is a flowchart illustrating an example of the operation that can be performed by the ophthalmic apparatus according to the exemplary embodiment.

FIG. 9 shows the first operation example of the ophthalmic apparatus 1A. In the present operation example, for example, a fixation target for macula imaging may be presented on the subject's eye E. In addition, preliminary alignment may be performed prior to step S21.

(S21: Change Arm Length to Obtain Signal of Cornea)

In the same manner as step S2 in the first embodiment, the scan controlling circuitry 450A (and the data processing circuitry 230) changes any one or both of the measurement arm length and the reference arm length to obtain a signal corresponding to the cornea of the subject's eye E.

(S22: Acquire First Deviation Information)

After the change of the arm length in step S21 has been completed, the deviation detector 420 performs the first deviation measurement corresponding to the first OCT scan (the anterior eye segment OCT scan) to acquire the first deviation information.

(S23: Apply OCT Scan to Anterior Eye Segment)

After the acquisition of the deviation information in step S22 has been completed, the scan controlling circuitry 450A performs control for applying an OCT scan to the anterior eye segment of the subject's eye E. In the present example, the scan controlling circuitry 450A performs the first scan control that causes the scanner 410 to perform an OCT scan on the anterior eye segment region including the corneal surface of the subject's eye E. Step S23 is performed in the same manner as step S3 in the first embodiment.

(S24: Generate Reflection Intensity Profile)

The scanner 410 (the image constructing circuitry 220 therein) generates a reflection intensity profile from the data acquired in the OCT scan in step S23. The reflection intensity profile generated is, for example, data corresponding to the A-line to which the A-scan is applied in step S23.

(S25: Record Retroreflector Position, Reflection Intensity Profile, and First Deviation Information)

In the same manner as step S5 in the first embodiment, the ophthalmic apparatus 1 (e.g., the distance calculating circuitry 460A) records the position of the retroreflector at the time of performing the OCT scan in step S23, and the reflection intensity profile generated in step S24. In addition, the ophthalmic apparatus 1 (e.g., the distance calculating circuitry 460A) records the first deviation information acquired in step S22.

(S26: Change Arm Length to Obtain Signal of Retina)

Next, the scan controlling circuitry 450A (and the data processing circuitry 230) changes any one or both of the measurement arm length and the reference arm length to obtain a signal corresponding to the retina of the subject's eye E.

(S27: Acquire Second Deviation Information)

After the adjustment of the arm length in step S26 has been completed, the deviation detector 420 performs the second deviation measurement corresponding to the second OCT scan (the posterior eye segment OCT scan) to acquire the second deviation information. This process is performed in the same manner as step S22.

(S28: Apply OCT Scan to Posterior Eye Segment)

After the acquisition of the deviation information in step S27 has been completed, the scan controlling circuitry 450A performs control for applying an OCT scan to the posterior eye segment of the subject's eye E. In the present example, the scan controlling circuitry 450A performs the second scan control that causes the scanner 410 to perform an OCT scan on the posterior eye segment region including the retinal surface of the subject's eye E.

(S29: Generate Reflection Intensity Profile)

The scanner 410 (the image constructing circuitry 220 therein) generates a reflection intensity profile from the data acquired in the OCT scan in step S28. The reflection intensity profile generated is, for example, data corresponding to the A-line to which the A-scan is applied in step S28.

(S30: Record Retroreflector Position, Reflection Intensity Profile, and Second Deviation Information)

In the same manner as step S25, the ophthalmic apparatus 1 (e.g., the distance calculating circuitry 460A) records the position of the retroreflector at the time of performing the OCT scan in step S28, the reflection intensity profile generated in step S29, and the second deviation information acquired in step S27.

(S31: Calculate Axial Length Considering First and Second Deviation Information)

The distance calculating circuitry 460A calculates the distance between the corneal surface and the retinal surface, based on the position of the retroreflector, the reflection intensity profile, and the first deviation information recorded in step S25, and on the position of the retroreflector, the reflection intensity profile, and the second deviation information recorded in step S30.

In the present example, the distance calculating circuitry 460A first calculates the difference between the first arm length and the second arm length (the arm length difference), based on the position of the retroreflector recorded in step S25 (that is, the first arm length applied to the anterior eye segment OCT scan), and on the position of the retroreflector recorded in step S30 (that is, the second arm length applied to the posterior eye segment OCT scan). Further, the distance calculating circuitry 460A analyzes the reflection intensity profile recorded in step S25 to specify a position corresponding to the corneal surface (the first position), and analyzes the reflection intensity profile recorded in step S30 to specify a position corresponding to the retinal surface (the second position). Then, the distance calculating circuitry 460A calculates the axial length of the subject's eye E, based on the first deviation information recorded in step S25 and the second deviation information recorded in step S30 in addition to the arm length difference, the first position, and the second position. This calculation is performed, for example, according to the method described in conjunction with FIG. 8. Note that this example considers both the alignment error in the anterior eye segment OCT scan and the alignment error in the posterior eye segment OCT scan. This terminates the operation according to the present operation example (End).

Second Operation Example

Figure 10:
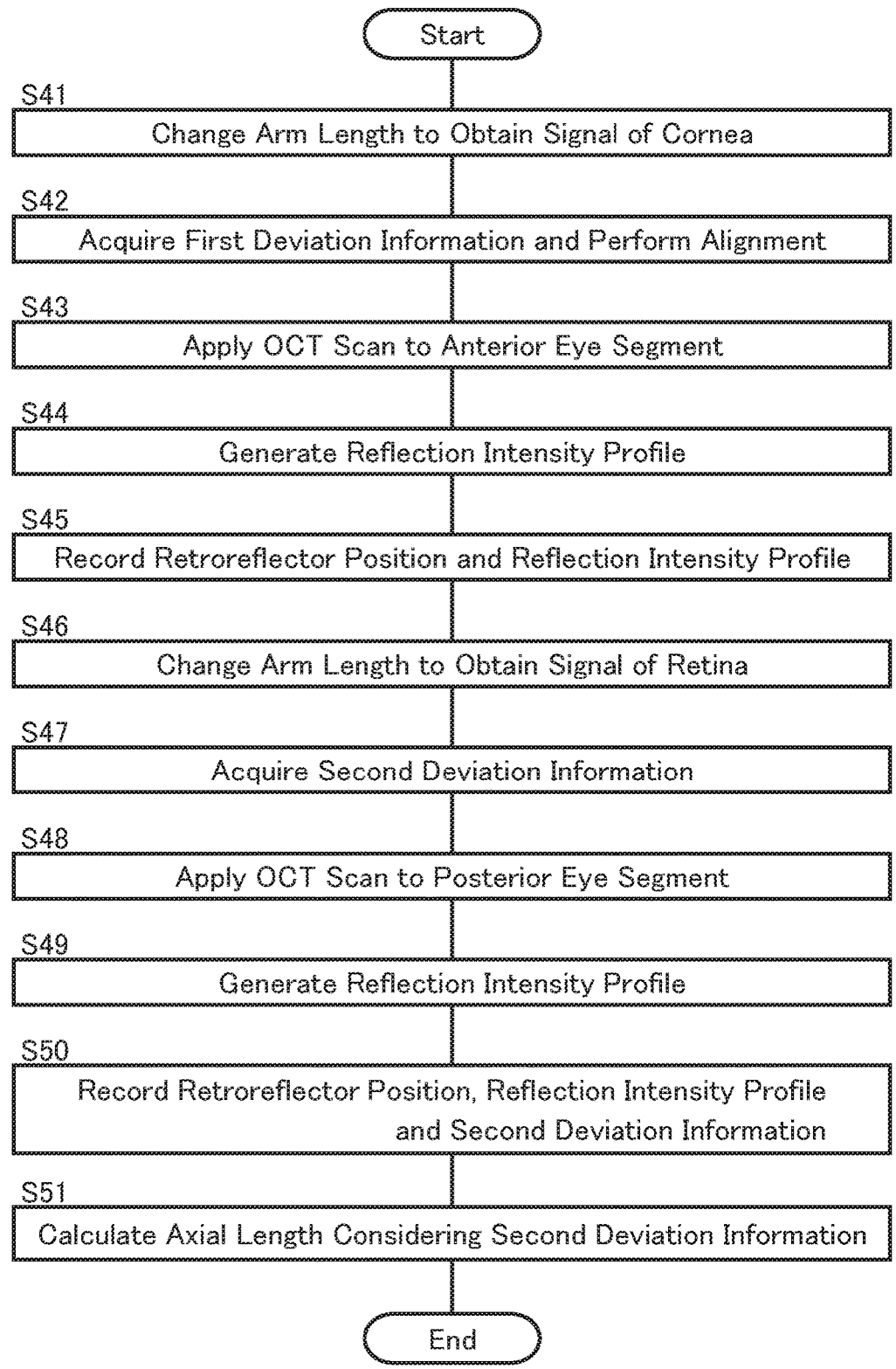
FIG. 10 is a flowchart illustrating an example of the operation that can be performed by the ophthalmic apparatus according to the exemplary embodiment.

FIG. 10 shows the second operation example of the ophthalmic apparatus 1A. In the present operation example, a fixation target for macula imaging may be presented on the subject's eye E, for example. In addition, preliminary alignment may be performed prior to step S41.

(S41: Change Arm Length to Obtain Signal of Cornea)

The scan controlling circuitry 450A (and the data processing circuitry 230) changes any one or both of the measurement arm length and the reference arm length to obtain a signal corresponding to the cornea of the subject's eye E.

(S42: Acquire First Deviation Information and Perform Alignment)

After the change of the arm length in step S41 has been completed, the deviation detector 420 performs the first deviation measurement corresponding to the first OCT scan (the anterior eye segment OCT scan) to acquire the first deviation information. The alignment controlling circuitry 440A performs alignment control that controls the movement mechanism 150 based on the first deviation information acquired. The alignment control is performed in the same manner as in the first embodiment.

(S43: Apply OCT Scan to Anterior Eye Segment)

After the alignment in step S42 has been completed, the scan controlling circuitry 450A performs control for applying an OCT scan to the anterior eye segment of the subject's eye E. In the present example, the scan controlling circuitry 450A performs the first scan control that causes the scanner 410 to perform an OCT scan on the anterior eye segment region including the corneal surface of the subject's eye E. It may be assumed that the anterior eye segment OCT scan is performed in an appropriate alignment condition.

(S44: Generate Reflection Intensity Profile)

The scanner 410 (the image constructing circuitry 220 therein) generates a reflection intensity profile from the data acquired in the OCT scan in step S43. The reflection intensity profile generated is, for example, data corresponding to the A-line to which the A-scan is applied in step S43.

(S45: Record Retroreflector Position and Reflection Intensity Profile)

The ophthalmic apparatus 1 (e.g., the distance calculating circuitry 460A) records the position of the retroreflector at the time of performing the OCT scan in step S43, and the reflection intensity profile generated in step S44.

(S46: Change Arm Length to Obtain Signal of Retina)

Next, the scan controlling circuitry 450A (and the data processing circuitry 230) changes any one or both of the measurement arm length and the reference arm length to obtain a signal corresponding to the retina of the subject's eye E.

(S47: Acquire Second Deviation Information)

After the adjustment of the arm length in step S46 has been completed, the deviation detector 420 performs the second deviation measurement corresponding to the second OCT scan (the posterior eye segment OCT scan) to acquire the second deviation information. Unlike the anterior eye segment OCT scan, which is assumed to be performed in an appropriate alignment condition, an appropriate alignment condition is not ensured in the posterior eye segment OCT scan. Therefore, only the second deviation information is taken into account in the distance calculation in the present example (described later in step S51).

(S48: Apply OCT Scan to Posterior Eye Segment)

After the acquisition of the deviation information in step S47 has been completed, the scan controlling circuitry 450A performs control for applying an OCT scan to the posterior eye segment of the subject's eye E. In the present example, the scan controlling circuitry 450A performs the second scan control that causes the scanner 410 to perform an OCT scan on the posterior eye segment region including the retinal surface of the subject's eye E.

(S49: Generate Reflection Intensity Profile)

The scanner 410 (the image constructing circuitry 220 therein) generates a reflection intensity profile from the data acquired in the OCT scan in step S48. The reflection intensity profile generated is, for example, data corresponding to the A-line to which the A-scan is applied in step S48.

(S50: Record Retroreflector Position, Reflection Intensity Profile, and Second Deviation Information)

The ophthalmic apparatus 1 (e.g., the distance calculating circuitry 460A) records the position of the retroreflector at the time of performing the OCT scan in step S48, the reflection intensity profile generated in step S49, and the second deviation information acquired in step S47.

(S51: Calculate Axial Length)

The distance calculating circuitry 460A calculates the distance between the corneal surface and the retinal surface, based on the position of the retroreflector and the reflection intensity profile recorded in step S45, as well as the position of the retroreflector, the reflection intensity profile, and the second deviation information recorded in step S50.

In the present example, the distance calculating circuitry 460A first calculates the difference between the first arm length and the second arm length (the arm length difference), based on the position of the retroreflector recorded in step S45 (that is, the first arm length applied to the anterior eye segment OCT scan), and the position of the retroreflector recorded in step S50 (that is, the second arm length applied to the posterior eye segment OCT scan). Further, the distance calculating circuitry 460A analyzes the reflection intensity profile recorded in step S45 to specify a position corresponding to the corneal surface (the first position), and analyzes the reflection intensity profile recorded in step S50 to specify a position corresponding to the retinal surface (the second position). Then, the distance calculating circuitry 460A calculates the axial length of the subject's eye E, based on the second deviation information recorded in step S50 in addition to the arm length difference, the first position, and the second position. This calculation is performed, for example, according to the method described in conjunction with FIG. 8. This terminates the operation according to the present operation example (End).

Modifications of the Second Embodiment

Some modifications applicable to the ophthalmic apparatus 1A according to the second embodiment will be described. Note that, unless otherwise mentioned, the reference symbols used in the description of the ophthalmic apparatus 1 and/or the ophthalmic apparatus 1A will be used in the following description.

First Modification Example

Similar to the first modification example of the first embodiment, the OCT scan may be applied to the posterior eye segment a plurality of times in order to cope with the adverse effect of the turbidity or floaters moving in the vitreous body on the posterior eye segment OCT scan. The repetitive OCT scan is performed by the scanner 410 under the control of the scan controlling circuitry 450A.

The scanner 410 generates a reflection intensity profile or image data from detection signals obtained by each of the plurality of OCT scans. Thereby, a data group (a plurality of pieces of data) corresponding to the plurality of OCT scans are obtained. The distance calculating circuitry 460A may acquire a single piece of data from the data group acquired by the plurality of OCT scans, and perform the distance calculation using the single piece of data acquired.

Second Modification Example

As in the second modification of the first embodiment, an OCT scan may be applied to a three dimensional region of the subject's eye E in order to accurately specify the two sites of the subject's eye E. For example, in any one or both of the anterior eye segment OCT scan and the posterior eye segment OCT scan, the scan controlling circuitry 450A causes the scanner 410 to perform an OCT scan on a three dimensional region of the subject's eye E.

The distance calculating circuitry 460A may specify the feature position corresponding to a feature point of the subject's eye E by analyzing the data acquired by the OCT scan on the three dimensional region of the subject's eye E, and then calculate the length of a line segment whose one end is placed at the feature position specified. The length of the line segment is the distance for the purpose of the measurement.

Effects

The effects of the ophthalmic apparatus 1A according to the second embodiment and the modification examples thereof will be described.

The ophthalmic apparatus 1A includes the scanner 410, the deviation detector 420, the scan controlling circuitry 450A, and the distance calculating circuitry 460A.

The scanner 410 is configured to apply an OCT scan to the subject's eye E. The deviation detector 420 is configured to measure the deviation of the subject's eye E with respect to a predetermined reference position.

The scan controlling circuitry 450A is configured to perform the first scan control and the second scan control. The first scan control causes the scanner 410 to perform an OCT scan on the first region (e.g., the anterior eye segment region) including the first site of the subject's eye E (e.g., the corneal surface). The second scan control causes the scanner 410 to perform an OCT scan on the second region (e.g., the posterior eye segment region) including the second site different from the first site (e.g., the retinal surface).

The distance calculating circuitry 460A is configured to calculate a distance between the first site and the second site of the subject's eye E (e.g., the axial length) based on the followings: at least one of the first deviation information of the subject's eye E acquired by the deviation detector 420 in response to the first scan control and the second deviation information of the subject's eye E acquired by the deviation detector 420 in response to the second scan control; the first data acquired by the scanner 410 under the first scan control; and the second data acquired by the scanner 410 under the second scan control.

According to the ophthalmic apparatus 1A configured as described above, the alignment error (the deviation information) in any one or both of the first OCT scan and the second OCT scan can be acquired, and the distance can be calculated in consideration of the alignment error(s). Therefore, for example, in the event of performing the second OCT scan after the first OCT scan, the reliability of the distance measurement can be secured even if the subject's eye moves during the period from the first OCT scan to the second OCT scan.

As an optional configuration, the deviation detector 420 may be configured to acquire one deviation information in response to one scan control from among the first scan control and the second scan control, and further acquire the other deviation information prior to the other scan control from among the first scan control and the second scan control. Further, the ophthalmic apparatus 1A may include the movement mechanism 150 and the alignment controlling circuitry 440A. The movement mechanism 150 is configured to move at least part of the scanner 410. The alignment controlling circuitry 440A is configured to perform alignment control of controlling the movement mechanism 150 based on the other deviation information prior to the other scan control. The distance calculating circuitry 460A may be configured to calculate the distance based on the one deviation information, the first data, and the second data.

For example, in the second operation example shown in FIG. 10, the deviation detector 420 acquires the first deviation information and performs alignment prior to the first scan control, and calculates the distance based on the second deviation information acquired in response to the second scan control, the first data, and the second data.

According to the optional configuration thus configured, one of the first OCT scan and the second OCT scan can be performed after alignment, and the distance can be calculated in consideration of the alignment error in the other OCT scan. Therefore, the distance measurement can be performed with high reliability.

As an optional configuration, the scanner 410 may include an interference optical system and an arm length changer. The interference optical system includes a measurement arm that guides the measurement light LS to the subject's eye E, and a reference arm that guides the reference light LR. The arm length changer is provided in at least one of the measurement arm and the reference arm, and changes the arm length under the control of the scan controlling circuitry 450A. The combination of the retroreflector 41 and the retroreflector driver 41A is an example of the arm length changer provided in the measurement arm. The combination of the retroreflector 114 and the retroreflector driver 114A is an example of the arm length changer provided in the reference arm.

In addition, as an optional configuration, the distance calculating circuitry 460A can perform the following series of processes: (1) the process of calculating the difference (arm length difference) between the first arm length applied at the time of the first scan control (the first OCT scan) and the second arm length applied at the time of the second scan control (the second OCT scan); (2) the process of analyzing the first data acquired in the first OCT scan to specify the first position corresponding to the first site of the subject's eye E (e.g., a signal position on the corneal surface); (3) the process of analyzing the second data acquired in the second OCT scan to specify the second position corresponding to the second site of the subject's eye E (e.g., a signal position on the retinal surface); and (4) the process of calculating the distance between the first site and the second site (e.g., the axial length) based on the arm length difference calculated in (1), the first position specified in (2), the second position specified in (3), and at least one of the first deviation information and the second deviation information acquired by the deviation detector 420.

Here, the distance calculating circuitry 460A may be configured as follows. First, the distance calculating circuitry 460A calculates a provisional distance between the first site and the second site based on the arm length difference, the first position, and the second position. Further, the distance calculating circuitry 460A calculates the distance between the first site and the second site based on the provisional distance, at least one of the first deviation information and the second deviation information, and the corneal curvature radius of the subject's eye E acquired in advance.

The following is a specific example of such a distance calculation: When the provisional distance between the first site and the second site is denoted by ALm, one of the first deviation information and the second deviation information is denoted by h, the corneal curvature radius is denoted by r, and the distance between the first site and the second site (the true value) is denoted by AL, the distance calculating circuitry 460A calculates the distance AL by using the following arithmetic formula: AL=(r−r*cos(arcsin(h/r)))+ALm*cos(arcsin(h/ALm)).

According to the optional configurations described above, specific and concrete processing for calculating the distance between the first site and the second site of the subject's eye E can be provided.

As an optional configuration, the scan controlling circuitry 450A may be configured to cause the scanner 410 to perform a plurality of OCT scans in at least one of the first scan control (the first OCT scan) and the second scan control (the second OCT scan). If this is the case, the distance calculating circuitry 460A can acquire a single piece of data from the data group acquired by the plurality of OCT scans. Here, the distance calculating circuitry 460A may be configured to generate the single piece of data by applying averaging calculation to the data group acquired by the plurality of OCT scans. Further, the distance calculating circuitry 460A may be configured to calculate the distance between the first site and the second site (e.g., the provisional distance mentioned above) using the single piece of data acquired.

According to the optional configuration configured in this way, even if the turbidity or floaters moving in the vitreous body adversely affects the posterior eye segment OCT scan, the noise caused by the turbidity or floaters can be reduced or eliminated, and/or, the data that is not affected by the turbidity or floaters or data that is less affected can be selected. This makes it possible to improve the reliability of the distance measurement.

As an optional configuration, the scan controlling circuitry 450A may be configured to cause the scanner 410 to perform an OCT scan on a three dimensional region of the subject's eye E in at least one of the first scan control (the first scan) and the second scan control (the second scan). If this is the case, the distance calculating circuitry 460A may be configured to analyze the data acquired by the OCT scan on the three dimensional region to specify a feature position corresponding to a feature point of the subject's eye E. In addition, the distance calculating circuitry 460A may be configured to calculate the length of a line segment whose one end is placed at the specified feature position, as the distance between the first site and the second site (e.g., the aforementioned provisional distance).

As the first typical example, the scan controlling circuitry 450A may be configured to cause the scanner 410 to perform an OCT scan on a three dimensional region including the corneal surface of the subject's eye E in the first scan control (the first OCT scan). In addition, the distance calculating circuitry 460A may be configured to analyze the data acquired by the OCT scan on the three dimensional region to specify a feature position corresponding to the corneal apex of the subject's eye E. If this is the case, the distance calculating circuitry 460A may be configured to calculate the length of a line segment whose one end is placed at the corneal apex, as the distance between the first site and the second site (e.g., the aforementioned provisional distance).

As the second typical example, the scan controlling circuitry 450A may be configured to cause the scanner to perform an OCT scan on a three dimensional region including the retinal surface of the subject's eye E in the second scan control (the second OCT scan). Further, the distance calculating circuitry 460A may be configured to analyze the data acquired by the OCT scan on the three dimensional region to specify a feature position corresponding to the macular center. Id this is the case, the distance calculating circuitry 460A may be configured to calculate the length of a line segment whose one end is placed at the macular center, as the distance between the first site and the second site (e.g., the aforementioned provisional distance).

By combining the first and second typical examples, the length of the line segment whose one end is placed at the corneal apex and the other end is placed at the macular center can be determined. That is, the axial length of the subject's eye E can be determined in this way.

As an optional configuration, the deviation detector 420 includes the alignment optical system 50 (a projection system), the two (or more) anterior eye segment cameras 300 (two or more cameras), and the deviation calculating circuitry 430. The alignment optical system 50 is configured to project a light beam onto the anterior eye segment of the subject's eye E. The two (or more) anterior eye segment cameras 300 are configured to photograph the anterior eye segment of the subject's eye E from mutually different directions. The deviation calculating circuitry 430 is configured to calculate the deviation of the subject's eye E with respect to a predetermined reference position based on positions of images of the light beam (bright spot images) in the two (or more) anterior eye segment images acquired by the two or more anterior eye segment cameras 300.

According to the optional configuration described above, a specific and concrete configuration and processing for measuring the deviation of the subject's eye E with respect to a predetermined reference position can be provided.

In addition, any of the items described in the second embodiment (configurations, elements, processing, processes, operations, actions, functions, etc.) and/or any of known items may be combined with the ophthalmic apparatus described in the present example. Further, any of the items described in the first embodiment (configurations, elements, processing, processes, operations, actions, functions, etc.) may be combined with the ophthalmic apparatus described in the present example.

The second embodiment provides a method of controlling an ophthalmic apparatus. The ophthalmic apparatus includes a scanner (410) configured to apply an OCT scan to the subject's eye E and a deviation detector (420) configured to measure the deviation of the subject's eye (E) with respect to a predetermined reference position.

The controlling method includes the first scan control step, the second scan control step, the deviation detection step, and the distance calculation step.

The first scan control step causes the scanner (410) to perform an OCT scan on the first region including the first site of the subject's eye (E). This OCT scan is referred to as the first OCT scan. Further, the second scan control step causes the scanner (410) to perform an OCT scan on the second region including the second site different from the first site of the subject's eye (E). This OCT scan is referred to as the second OCT scan.

The deviation detection step causes the deviation detector (420) to perform at least one of the step of acquiring the first deviation information of the subject's eye (E) in response to the first scan control, and the step of acquiring the second deviation information of the subject's eye (E) in response to the second scan control.

The distance calculation step calculates the distance between the first site and the second site of the subject's eye (E), based on at least one of the first deviation information and the second deviation information acquired in the deviation detection step, the first data acquired by the scanner (410) in the first scan control step, and the second data acquired by the scanner (410) in the second scan control step.

According to the controlling method of ophthalmic apparatus as described above, it is possible to obtain an alignment error (deviation information) in any one or both of the first OCT scan and the second OCT scan, and to calculate the distance in consideration of the alignment error(s). Therefore, the reliability of the distance measurement can be secured.

Note that any of the items described in the first embodiment (configurations, elements, processing, processes, operations, actions, functions, etc.), and/or, any of the items described in the second embodiment (configurations, elements, processing, processes, operations, actions, functions, etc.), and/or, any of known items may be combined with the controlling method of the present example.

A program that causes a computer to execute such a controlling method may be configured. The program may include, for example, any of the aforementioned programs for operating the ophthalmic apparatus 1A of the second embodiment or a modification example thereof.

Further, it is possible to create a computer readable non-transitory recording medium storing such a program. The non-transitory recording medium may be in any form or aspect, and examples thereof include magnetic disks, optical disks, magneto-optical disks, semiconductor memories and the like.

<Other Items>

The aspects described above are merely illustrative of the implementation of the present invention. A person who intends to practice the present invention may apply any modification (omission, substitution, replacement, addition, etc.) within the scope of the present invention.

For example, the ophthalmic apparatus according to some embodiments may have a configuration for measuring a characteristic of the subject's eye. As a specific example, the ophthalmic apparatus according to some embodiments may have a configuration for measuring the corneal curvature radius of the subject's eye. The configuration for the corneal curvature radius measurement may include an optical system, an arithmetic system, and a control system that have the same configurations as those of a conventional corneal shape measuring apparatus. An example of the configuration for measuring the corneal curvature radius includes the configuration using a kerato plate (kerato ring) or a placido plate (placido ring) disclosed in Japanese Unexamined Patent Application Publication No. 2017-063978 filed by the present applicant. The corneal curvature radius may be measured by using an anterior eye segment OCT scan, instead. Note that the configuration for measuring the corneal curvature radius is not limited to these examples, and may be a configuration using any known technique.

The characteristics of the subject's eye that can be measured by the ophthalmic apparatus according to some embodiments are not limited to the corneal curvature radius. For example, the ophthalmic apparatus according to some embodiments may have a configuration for measuring the refractive power of the subject's eye (e.g., spherical power, astigmatic power, and/or astigmatism axis angle). The configuration for measuring the refractive power of the subject's eye may include an optical system, an arithmetic system, and a control system that have the same configurations as a conventional refractive power measuring apparatus (a refractometer). An example of the configuration for measuring the refractive power includes the configuration disclosed in Japanese Unexamined Patent Application Publication No. 2017-063978 filed by the present applicant.

When the ophthalmic apparatus according to some embodiments has the eye refractive power measuring function, the ophthalmic apparatus may be configured to use the eye refractive power measuring function, in place of using the focus optical system 60 as described in the above disclosure, to determine the focal position. Then, the ophthalmic apparatus may move the OCT focusing lens 43 to focus on the focal position determined.

In the above-mentioned disclosure, the method using the alignment indicator and the method using the anterior eye segment cameras have been described as the applicable alignment method. However, other alignment methods may be applied. An example of the other alignment methods is a method using an optical lever. The alignment method of ophthalmic apparatus using the optical lever is disclosed, for example, in Japanese Unexamined Patent Application Publication No. 2012-148032 and Japanese Unexamined Patent Application Publication No. 2018-050922.

The deviation detector of the ophthalmic apparatus of the present example is configured to measure the deviation of the subject's eye with respect to a predetermined reference position by using the optical lever. The predetermined reference position is, for example, the position corresponding to the working distance. In other words, the predetermined reference position is the position separated in the z direction from the subject's eye by the predetermined working distance, and the deviation measured is typically a deviation in the z direction.

The deviation detector in the present example includes a projection system that projects a light beam obliquely onto the anterior eye segment of the subject's eye and an image sensor that detects reflection of the light beam of the projected light beam from the anterior eye segment. The configurations and arrangement of the projection system and the image sensor may be the same as those of a conventional optical lever alignment means.

A typical projection system includes a light source and a lens. The optical axis of the typical projection system is tilted by the first angle in the first direction with respect to the optical axis of the measurement arm (the optical axis of the objective lens). A typical image sensor may be a CCD image sensor or a CMOS image sensor, and may be a line sensor or an area sensor. Typically, an imaging lens is disposed between the image sensor and the subject's eye E. The optical axis of the detection system including the image sensor and the imaging lens is tilted by the second angle in the second direction with respect to the optical axis of the measurement arm. Here, the second angle is equal to the first angle, and the second direction is opposite to the first direction.

With such a configuration and arrangement, when the projection system and the detection system are located within a predetermined area with respect to the subject's eye, the image sensor can detect the reflection of the light beam. In addition, the change in the relative position of the projection system and the detection system with respect to the subject's eye, induces the change in the detection position of the reflection of the light beam by the image sensor changes. In other words, the position of the reflection of the light beam projected on the light receiving area (e.g., the light receiving element array) of the image sensor varies according to the relative position of the projection system and the detection system with respect to the subject's eye.

The deviation detector of the present example includes the deviation calculating circuitry that calculates the deviation of the subject's eye based on the position of the reflection detected by the image sensor. The calculation executed by the deviation calculating circuitry of the present example may be the same as the calculation performed by the conventional optical lever type alignment method, and, typically, the deviation in the z direction is detected. The deviation calculating circuitry of the present example is realized by the cooperation of hardware including a circuit (circuitry) and deviation calculating software.

According to the present example, a specific and concrete configuration and processing for measuring the deviation of the subject's eye with respect to a predetermined reference position can be provided as in the case of using the alignment indicator or using two or more anterior eye segment cameras.

While certain embodiments have been described, these embodiments have been presented by way of example only, and are not intended to limit the scope of the inventions. Indeed, the novel embodiments described herein may be embodied in a variety of other forms; furthermore, various omissions, substitutions, additions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmic apparatus comprising:
    a scanner that applies an optical coherence tomography (OCT) scan to a subject's eye;
    a movement mechanism that moves at least part of the scanner;
    a deviation detector that measures deviation of the subject's eye with respect to a predetermined reference position;
    scan controlling circuitry that performs first scan control of causing the scanner to perform an OCT scan on a first region including a first site of the subject's eye, and second scan control of causing the scanner to perform an OCT scan on a second region including a second site different from the first site;
    alignment controlling circuitry that performs first alignment control of controlling the movement mechanism based on first deviation information of the subject's eye acquired by the deviation detector prior to the first scan control, and second alignment control of controlling the movement mechanism based on second deviation information of the subject's eye acquired by the deviation detector prior to the second scan control; and
    distance calculating circuitry that calculates a distance between the first site and the second site based on first data acquired by the scanner under the first scan control and second data acquired by the scanner under the second scan control, wherein
    the scanner includes:
        an interference optical system that includes a measurement arm that guides measurement light to the subject's eye and a reference arm that guides reference light; and
        an arm length changer that is provided in at least one of the measurement arm and the reference arm, and changes an arm length under control of the scan controlling circuitry, and
    the distance calculating circuitry calculates a difference between a first arm length applied at a time of the first scan control and a second arm length applied at a time of the second scan control, analyzes the first data to specify a first position corresponding to the first site, analyzes the second data to specify a second position corresponding to the second site, and calculates the distance based on the difference, the first position, and the second position.

2. An ophthalmic apparatus comprising:
a scanner that applies an optical coherence tomography (OCT) scan to a subject's eye;
a deviation detector that measures deviation of the subject's eye with respect to a predetermined reference position;
scan controlling circuitry that performs first scan control of causing the scanner to perform an OCT scan on a first region including a first site of the subject's eye, and second scan control of causing the scanner to perform an OCT scan on a second region including a second site different from the first site; and
distance calculating circuitry that calculates a distance between the first site and the second site, based on at least one of first deviation information of the subject's eye acquired by the deviation detector in response to the first scan control and second deviation information of the subject's eye acquired by the deviation detector in response to the second scan control, first data acquired by the scanner under the first scan control, and second data acquired by the scanner under the second scan control, wherein
the scanner includes:
an interference optical system that includes a measurement arm that guides measurement light to the subject's eye, and a reference arm that guides reference light; and
an arm length changer that is provided in at least one of the measurement arm and the reference arm, and changes an arm length under control of the scan controlling circuitry, and
the distance calculating circuitry calculates a difference between a first arm length applied at a time of the first scan control and a second arm length applied at a time of the second scan control, analyzes the first data to specify a first position corresponding to the first site, analyzes the second data to specify a second position corresponding to the second site, and calculates the distance based on the difference, the first position, the second position, and at least one of the first deviation information and the second deviation information.

3. The ophthalmic apparatus of claim 2,
wherein the distance calculating circuitry calculates a provisional distance between the first site and the second site based on the difference, the first position, and the second position, and calculates the distance based on the provisional distance, at least one of the first deviation information and the second deviation information, and corneal curvature radius of the subject's eye acquired in advance, and
wherein when the provisional distance is denoted by ALm, one of the first deviation information and the second deviation information is denoted by h, the corneal curvature radius is denoted by r, and the distance is denoted by AL, the distance calculating circuitry calculates the distance AL by using an arithmetic formula $$AL = (r - r^* \cos(\arcsin(h/r))) + ALm^* \cos(\arcsin(h/ALm)).$$

4. A method of controlling an ophthalmic apparatus that includes a scanner configured to apply an optical coherence tomography (OCT) scan to a subject's eye, a movement mechanism configured to move at least part of the scanner, and a deviation detector configured to measure deviation of the subject's eye with respect to a predetermined reference position, the method comprising:

a first alignment control step that controls the movement mechanism based on first deviation information of the subject's eye acquired by the deviation detector;
a first scan control step that causes the scanner to perform an OCT scan on a first region including a first site of the subject's eye;
a second alignment control step that controls the movement mechanism based on second deviation information of the subject's eye acquired by the deviation detector;
a second scan control step that causes the scanner to perform an OCT scan on a second region including a second site different from the first site; and
a distance calculation step that calculates a distance between the first site and the second site, based on first data acquired by the scanner in the first scan control step and second data acquired by the scanner in the second scan control step, wherein
the scanner includes:
an interference optical system that includes a measurement arm that guides measurement light to the subject's eye, and a reference arm that guides reference light; and
an arm length changer that is provided in at least one of the measurement arm and the reference arm, and changes an arm length under control of the scan controlling circuitry, and
the distance calculation step calculates a difference between a first arm length applied at a time of the first scan control step and a second arm length applied at a time of the second scan control step, analyzes the first data to specify a first position corresponding to the first site, analyzes the second data to specify a second position corresponding to the second site, and calculates the distance based on the difference, the first position, the second position, and at least one of the first deviation information and the second deviation information.

5. A method of controlling an ophthalmic apparatus that includes a scanner configured to apply an optical coherence tomography (OCT) scan to a subject's eye, and a deviation detector configured to measure deviation of the subject's eye with respect to a predetermined reference position, the method comprising:

a first scan control step that causes the scanner to perform an OCT scan on a first region including a first site of the subject's eye;
a second scan control step that causes the scanner to perform an OCT scan on a second region including a second site different from the first site;
a deviation detection step that causes the deviation detector to perform at least one of acquisition of first deviation information of the subject's eye in response to the first scan control, and acquisition of second deviation information of the subject's eye in response to the second scan control; and
a distance calculation step that calculates a distance between the first site and the second site, based on at least one of the first deviation information and the second deviation information acquired in the deviation detection step, first data acquired by the scanner in the first scan control step, and second data acquired by the scanner in the second scan control step, wherein the scanner includes:
- an interference optical system that includes a measurement arm that guides measurement light to the subject's eye, and a reference arm that guides reference light; and
- an arm length changer that is provided in at least one of the measurement arm and the reference arm, and changes an arm length under control of the scan controlling circuitry, and the distance calculation step calculates a difference between a first arm length applied at a time of the first scan control step and a second arm length applied at a time of the second scan control step, analyzes the first data to specify a first position corresponding to the first site, analyzes the second data to specify a second position corresponding to the second site, and calculates the distance based on the difference, the first position, the second position, and at least one of the first deviation information and the second deviation information.

6. A computer-readable non-transitory recording medium storing a program that causes a computer to execute the method of claim 4.

7. A computer-readable non-transitory recording medium storing a program that causes a computer to execute the method of claim 5.

8. The method of claim 5, wherein the distance calculation step calculates a provisional distance between the first site and the second site based on the difference, the first position, and the second position, and calculates the distance based on the provisional distance, at least one of the first deviation information and the second deviation information, and corneal curvature radius of the subject's eye acquired in advance, and wherein when the provisional distance is denoted by $ALm$, one of the first deviation information and the second deviation information is denoted by $h$, the corneal curvature radius is denoted by $r$, and the distance is denoted by $AL$, the distance calculation step calculates the distance $AL$ by using an arithmetic formula $$AL = (r - r^*\cos(\arcsin(h/r))) + ALm^*\cos(\arcsin(h/ALm)).$$

9. A computer-readable non-transitory recording medium storing a program that causes a computer to execute the method of claim 8.

* * * * *